(12) United States Patent
Schmidt

(10) Patent No.: US 7,079,882 B1
(45) Date of Patent: Jul. 18, 2006

(54) METHOD AND APPARATUS FOR QUANTIFYING NERVE AND NEURAL-MUSCULAR INTEGRITY RELATED TO PELVIC ORGANS OR PELVIC FLOOR FUNCTIONS

(76) Inventor: Richard Schmidt, 4200 E. 9$^{th}$ Ave., Denver, CO (US) 80262

( * ) Notice: Subject to any disclaimer, the term of this patent is extended or adjusted under 35 U.S.C. 154(b) by 0 days.

(21) Appl. No.: 09/490,175

(22) Filed: Jan. 22, 2000

(51) Int. Cl.
*A61B 5/04* (2006.01)

(52) U.S. Cl. .................. 600/373; 600/546; 607/117; 607/138

(58) Field of Classification Search ............... 7/138; 128/DIG. 25; 600/373, 377, 546, 547, 554, 600/591
See application file for complete search history.

(56) References Cited

U.S. PATENT DOCUMENTS

| | | | |
|---|---|---|---|
| 3,635,212 A | 1/1972 | Watanabe et al. ............... | 128/2 |
| 3,640,284 A | 2/1972 | De Langis .................. | 128/422 |
| 3,650,275 A | 3/1972 | Von Der Mozel .......... | 128/407 |
| 3,920,003 A | 11/1975 | Ash et al. ................. | 128/2.1 Z |
| 3,933,147 A | 1/1976 | Du Vall et al. ............. | 128/2 S |

(Continued)

FOREIGN PATENT DOCUMENTS

| | | |
|---|---|---|
| DE | 2 043 105 | 3/1972 |
| DE | 39 19 453 A1 | 12/1989 |
| EP | 0 938 911 A2 | 1/1999 |
| FR | 2 693 113 A1 | 1/1994 |
| FR | 2 709 422 A1 | 3/1995 |
| WO | WO 90/12617 | 11/1990 |
| WO | WO 94/28792 | 12/1994 |
| WO | WO 97/36643 | 10/1997 |
| WO | WO 98/15318 | 4/1998 |

*Primary Examiner*—Linda C. M. Dvorak
*Assistant Examiner*—David M. Ruddy
(74) *Attorney, Agent, or Firm*—Kurt Kinghorn, Esq.

(57) ABSTRACT

The present invention is a method and apparatus for quantifying nerve and neural-muscular integrity related to pelvic organs or pelvic floor functions. In one embodiment, the invention is a method and device to measure muscle or nerve activity in the pelvis or pelvic floor. In a modification of this embodiment, the invention includes means for inducing an efferent nerve signal in the spinal cord or sacral nerves and then measuring the resulting nerve activity of the nerves of the pelvic floor region. In a preferred embodiment, the invention includes placing a probe in the anal canal or vagina, the probe having proximal recording electrodes along its outer surface. In one possible embodiment, the probe has a distensible sheath having recording electrodes located on its outside surface. In another embodiment, the probe has an inflatable balloon at its distal end with recording electrodes located on the outside surface of the inflatable balloon. In a further embodiment, the proximal recording electrodes will be located on the outside of the distal end of the probe itself. In yet another embodiment, a disk having recording electrodes is placed in the rectum in contact with the tissue above the submucous space. In yet another embodiment of the invention, an essentially "C" shaped clip is provided having a core made of a spring-like material.

15 Claims, 27 Drawing Sheets

U.S. PATENT DOCUMENTS

| | | | |
|---|---|---|---|
| 3,943,938 A | 3/1976 | Wexler et al. | 128/421 |
| 4,153,059 A | 5/1979 | Fravel et al. | 128/422 |
| 4,224,949 A | 9/1980 | Scott et al. | 128/734 |
| 4,279,256 A | 7/1981 | Bucalo | 128/419 R |
| 4,396,019 A | 8/1983 | Perry, Jr. | 128/733 |
| 4,406,288 A | 9/1983 | Horwinski et al. | 128/422 |
| 4,515,167 A | 5/1985 | Hochman | 128/736 |
| 4,607,639 A | 8/1986 | Tanagho et al. | 128/419 E |
| 4,687,002 A | 8/1987 | Lahr | |
| 4,688,581 A | 8/1987 | Moss | |
| 4,703,755 A | 11/1987 | Tanagho et al. | 128/419 R |
| 4,739,764 A | 4/1988 | Lue et al. | 128/419 R |
| 4,739,767 A | 4/1988 | Lahr | |
| 4,765,331 A | 8/1988 | Petruzzi et al. | 128/303.14 |
| 4,771,779 A | 9/1988 | Tanagho et al. | 128/419 E |
| 4,881,526 A | 11/1989 | Johnson et al. | 128/24.5 |
| 4,909,263 A | 3/1990 | Norris | 128/788 |
| 5,005,586 A | 4/1991 | Lahr | |
| 5,010,895 A | 4/1991 | Maurer et al. | 128/788 |
| 5,046,511 A | 9/1991 | Maurer et al. | 128/788 |
| 5,117,840 A | 6/1992 | Brenman et al. | 128/788 |
| 5,154,177 A | 10/1992 | Eisman et al. | 128/642 |
| 5,188,122 A | 2/1993 | Phipps et al. | |
| 5,199,430 A | 4/1993 | Fang et al. | 128/419 E |
| 5,199,443 A | 4/1993 | Maurer et al. | 128/788 |
| 5,259,388 A | 11/1993 | Eisman et al. | 128/733 |
| 5,314,465 A | 5/1994 | Maurer et al. | 607/138 |
| 5,370,671 A | 12/1994 | Maurer et al. | 607/41 |
| 5,376,206 A | 12/1994 | Maurer et al. | 156/242 |
| 5,385,577 A | 1/1995 | Maurer et al. | 607/41 |
| 5,411,548 A | 5/1995 | Carman | 607/138 |
| 5,423,329 A | 6/1995 | Ergas | 128/733 |
| 5,433,216 A | 7/1995 | Sugrue et al. | |
| 5,452,719 A | 9/1995 | Eisman et al. | 128/640 |
| 5,464,448 A | 11/1995 | Malewicz | 607/138 |
| 5,562,717 A | 10/1996 | Tippey et al. | 607/41 |
| 5,649,976 A | 7/1997 | Malewicz | 607/138 |
| 5,667,615 A | 9/1997 | Maurer et al. | 156/242 |
| 5,697,966 A | 12/1997 | Boutos | 607/138 |
| 5,702,428 A | 12/1997 | Tippey et al. | 607/41 |
| 5,704,908 A | 1/1998 | Hofmann et al. | |
| 5,722,419 A | 3/1998 | Semmlow et al. | |
| 5,759,471 A | 6/1998 | Malewicz | 264/250 |
| 5,782,902 A | 7/1998 | Boutos | 607/143 |
| 5,800,501 A | 9/1998 | Sherlock | 607/138 |
| D407,157 S | 3/1999 | Malewicz | D24/141 |
| 5,875,778 A | 3/1999 | Vroegop | |
| 5,911,649 A | 6/1999 | Miller | 600/372 |
| 5,924,984 A | 7/1999 | Rao | 600/373 |
| D415,835 S | 10/1999 | Malewicz | D24/187 |
| 5,978,712 A | 11/1999 | Suda et al. | 607/41 |
| 5,988,169 A | 11/1999 | Anderson et al. | 128/830 |
| 5,999,855 A | 12/1999 | DiMarco | |
| 6,030,375 A | 2/2000 | Anderson et al. | |
| 6,185,465 B1 | 2/2001 | Mo et al. | |
| 6,240,315 B1 | 5/2001 | Mo et al. | |
| 6,321,116 B1 * | 11/2001 | Mo et al. | 600/546 |

* cited by examiner

METHOD AND APPARATUS FOR QUANTIFYING NERVE AND NEURAL-MUSCULAR INTEGRITY RELATED TO PELVIC ORGANS OR PELVIC FLOOR FUNCTIONS

FIELD OF THE INVENTION

The present invention relates to a method and apparatus for quantifying nerve and neural-muscular integrity related to pelvic organs or pelvic floor functions.

BACKGROUND OF THE INVENTION

The term "pelvic floor dysfunction" refers to a group of medical conditions generally related to organs and nerves of the pelvic floor area of the body. Some of these conditions include, but are not limited to urinary incontinence, urinary frequency, eneurisis, urethral syndrome, bladder neck disorder, bladder stones, reflux, prostate disorders, anal incontinence, encopresis, orchalgia, pelvic organ prolapse, sexual dysfunction, anal fissures, hemorrhoids, prostatodynia conditions, RUTI (recurrent urinary tract infection), chronic constipation syndromes, IC (intersticial cystitis), pelvic pain syndromes, vulvadynia and spastic colon. This list is not intended to be exhaustive. Instead, this list is intended to convey a number of conditions related to the nerves and organs of the pelvic floor area.

Pelvic floor dysfunction medical conditions are relatively common. For example, the National Institutes of Health (NIH) estimates that at least one-third of adult women are affected by at least one of these conditions.

Medical conditions resulting from pelvic floor dysfunction produce symptoms that often are embarrassing and uncomfortable. As a result, people with pelvic floor dysfunctions are often very uncomfortable talking about or seeking treatment for their condition. Their medical condition itself coupled with their reluctance to seek medical help often results in a lessened quality of life for the person with the medical condition and a lessened quality of life for their friends and families.

As stated, one example of a pelvic floor dysfunction medical condition is urinary incontinence. Urinary incontinence is the involuntary release of urine. The NIH estimates that 13 million people in the US experience urinary incontinence. Their studies show that women experience urinary incontinence twice as often as men. Further, older women are more likely to experience urinary incontinence than younger women. Urinary incontinence may result from many causes including neurogenic diseases such as multiple sclerosis, Parkinson's disease or Alzheimer's disease, strokes, brain tumors, congenital birth defects, weakening of pelvic floor muscles due to childbirth, injuries from accidents or as a side effect of medication or surgery.

Urinary incontinence manifests itself in at least the following ways: stress incontinence (the most common form of urinary incontinence); urge incontinence; overflow incontinence; total incontinence and enuresis. Stress incontinence is the leakage of urine when coughing, sneezing, laughing, jogging or doing anything that causes the person's abdominal pressure to be greater than the bladder's closure mechanism.

Urge incontinence is a sudden, strong desire to urinate along with a sudden, uncontrollable rush or leakage of urine. People suffering with urge incontinence may experience these symptoms at any time. For example, urge incontinence may manifest itself at any time during the day while doing normal activities or during sleep. Further, urinary incontinence may manifest itself after doing such innocuous tasks as drinking a small amount of water, touching water or hearing water running, as for example, when hearing someone else take a shower or wash dishes.

In 1998, T. H. Wagner and T. W. Hu estimated the cost of urinary incontinence for individuals 65 years and older in the US alone at $26.3 billion. This amounts to a cost of $3565 per individual with urinary incontinence or about $95 for every US inhabitant! (Wagner, T. H. and Hu, T. W., Economic Costs of Urinary Incontinence in 1995, UROLOGY, March, 1998, p 355–61).

Another pelvic floor dysfunction medical condition is anal incontinence. Anal incontinence is the inability to control bowel movements. Anal incontinence can manifest itself as the involuntary and unwanted passage of gas, liquid or solid stool. The overall prevalence of fecal incontinence has been reported to approach 20 percent. Further, between 12 and 39 percent of women following childbirth reported fecal or flatal incontinence.

Although specific pelvic floor dysfunction medical conditions have been mentioned above, the invention and its description relate to any and all conditions of the pelvic floor region involving nerve activity.

The terminal part of the human intestines is shown in FIG. 1 generally labeled 2. The terminal part 2 comprises a rectum 4 and an anal canal 6. Anal canal 6 begins at the anal verge 8 and continues into the body until reaching the submucous space 10. The anal crypt 12 is located at the terminal part 2 near the beginning of the submucous space 10. Physiologically, there is a groove 14 at the anal crypt 12.

Rectum 4 begins at the anal canal 6. A sphincter 16 surrounds the hemorrhoidal plexus 18 and puts pressure on the hemorrhoidal plexus 18 to form a seal at the base of the anal canal 6. The hemorrhoidal plexus 18 extends inwardly from the sphincter 16. Immediately "upstream" from the hemorrhoidal plexus 18, rectum 4 widens at 20.

The levator ani muscles 22 generally run from the front to back of the pubic bone 24 and helps to form the pelvic floor (FIG. 2). The levator ani muscles 22 provides support for the structures of the terminal part 2.

The rectum 4 contains a series of rectal valves: the inferior rectal valve 26, the middle rectal valve 28 and the superior rectal valve 30. These rectal valves 26, 28 and 30 are essentially folds in the inner surface of the rectum 4 and extend inwardly from the inner surface of the rectum 4. The inferior and superior rectal valves 26, 30 are located on one side of the rectum 4 while the middle rectal valve 28 is on the opposite side of the rectum 4 than are the inferior and superior rectal valves 26, 30.

As shown in FIG. 3, the pelvis and lower pelvic region is primarily innervated by sacral nerves, and more specifically the S2, S3 and S4 sacral nerves 32, 34 and 36, respectively. Both nerve impulses coming from nerve receptors in the pelvic region (afferent nerve impulses) and nerve impulses going to muscles and organs in the lower pelvic region (efferent nerve impulses) pass through sacral nerves 32, 34 and 36. In particular, it has been found that efferent nerve impulses through the sacral nerves 32, 34 and 36 affect the proper operation of the organs and systems of the pelvis and lower pelvic region including the urinary and fecal systems.

Skin tissue generally and specifically outside the submucous space 10 has karetin in it. As a result, the impedance of this tissue is quite hugh. This renders it difficult to detect electrical activity related to the nerve or muscle activity in the pelvic floor by recording electrodes placed on the skin.

Tissue in the anal canal 6 above the submucous space 10 does not have karetin in it. Consequently, the impedance of this tissue is relatively low compared to skin tissue. Therefore, it should be easier to detect electrical activity related to the nerve or muscle activity in the pelvic floor through recording electrodes placed on the surface of this tissue than it is to detect electrical activity through skin.

It is believed that many problems with such systems stem from improper nerve interaction with muscles and organs associated with the urinary and fecal systems. It would be highly desirable to be able to assess the condition of the nerves of the pelvic floor including the sacral nerves and the conduction of efferent and afferent nerve signals through the nerves of the pelvic floor.

SUMMARY OF THE INVENTION

The present invention is a method and apparatus for quantifying nerve and a neural-muscular integrity related to pelvic organs or pelvic floor functions. In one embodiment, the invention is a method and device to measure muscle or nerve activity in the pelvis or pelvic floor. In a modification of this embodiment, the invention includes means for inducing an efferent nerve signal in the spinal cord or sacral nerves and then measuring the resulting nerve activity of the nerves of the pelvic floor region.

In a preferred embodiment, the invention includes placing a probe in the anal canal, the probe having proximal recording electrodes along its outer surface. In one possible embodiment, the probe has a distensible sheath having recording electrodes located on its outside surface. The distensible sheath is moved outwardly away from a central axis so that the recording electrodes can be brought into contact with mucosal tissue of the rectal wall which in turn is pushed against the levator ani muscles for intimate contact. The distensible sheath is preferably moved outwardly by inflating a balloon located within the sheath.

In another embodiment, the probe has an inflatable balloon at its distal end with recording electrodes located on the outside surface of the inflatable balloon. The probe is place in the rectum and the inflatable balloon inflated so that the recording electrodes are moved into contact with the rectal wall which in turn is pushed against the surface of the levator ani muscles.

In a further embodiment, the proximal recording electrodes will be located on the outside of the distal end of the probe itself. The distal end of the probe is placed in the rectum and positioned so that the proximal recording electrodes come into contact with the rectum.

In yet another embodiment, a disk having recording electrodes is placed in the rectum in contact with the tissue above the submucous space. Preferably, the disk is placed in the groove near the anal crypt. In a slight variant of the embodiments described above, the invention may be placed in the vagina instead of or in addition to placing the invention in the rectum as described above. In the latter, it is preferable to have two devices, one for insertion into the rectum and one for insertion into the vagina.

In yet another embodiment of the invention, an essentially "C" shaped clip is provided having a core made of a spring-like material. The spring-like material biases the clip to remain in the "C" shaped configuration even if the clip is distended from its relaxed or unbiased configuration. Recording electrodes are placed on the inside surface of the clip. In use, the clip is either placed in the anal canal or in both the anal canal and vagina. The clip is distended slightly so that there is "pinching" pressure to hold the clip in place against tissue.

In a variant of the embodiments described above, recording electrodes may also be placed in the urethra. In one variant of this embodiment, a ring having recording electrodes is placed around a catheter such as a Foley catheter that is placed in the urethra. The recording electrodes contact the mucous tissue of the urethra to detect electrical activity. The recorded electrical information thus recorded may be evaluated independently or compared to the electrical activity detected by the recording electrodes placed in the rectum or vagina.

In any of the embodiments, the recording electrodes will come into contact with the mucous tissue of the rectum, vagina or urethra. Nerve activity in the pelvis or pelvic floor will be manifest as electrical activity that will be detected by the recording electrodes.

A predetermined property of the detected nerve electrical activity may be measured such as the amplitude of the detected electrical activity or the total electrical energy detected by the proximal recording electrodes. For example, the electrical activity due to nerve activity in the pelvic floor that is detected by the recording electrodes may be integrated over a window of time in order to determine the condition of the nerves of the pelvis or pelvic floor region.

In one embodiment, the invention also contemplates stimulating either the spinal cord or selected sacral nerves to produce an action potential in the nerves of the pelvis or pelvic floor region. This action potential will manifest itself as electrical activity that is then detected by the recording electrodes. By determining the amplitude and location of the nerve activity detected by the recording electrodes, the physician can determine the condition of the nerves innervating the pelvic floor or lower pelvic region.

In another embodiment, a stimulation driver generates a stimulation pulse having a predetermined pulse period and a predetermined amplitude. An implanted stimulation electrode delivers the pulse to the spinal cord or to a sacral nerve to produce afferent and/or efferent action potentials in the nerves of the spinal cord or sacral nerves. A recording electrode according to the invention is placed in the rectum in contact with the tissue of the rectum. The recording electrode receives electrical signals due to the action potentials created in response to the stimulation produced by the stimulating electrode. The timing of the detected response after the application of the stimulation pulse is determined.

These and other advantages and features of the invention will become apparent upon reading the following detailed description and referring to the accompanying drawings in which like reference numbers refer to like elements wherever found.

DETAILED DESCRIPTION OF THE INVENTION

Figure 1:
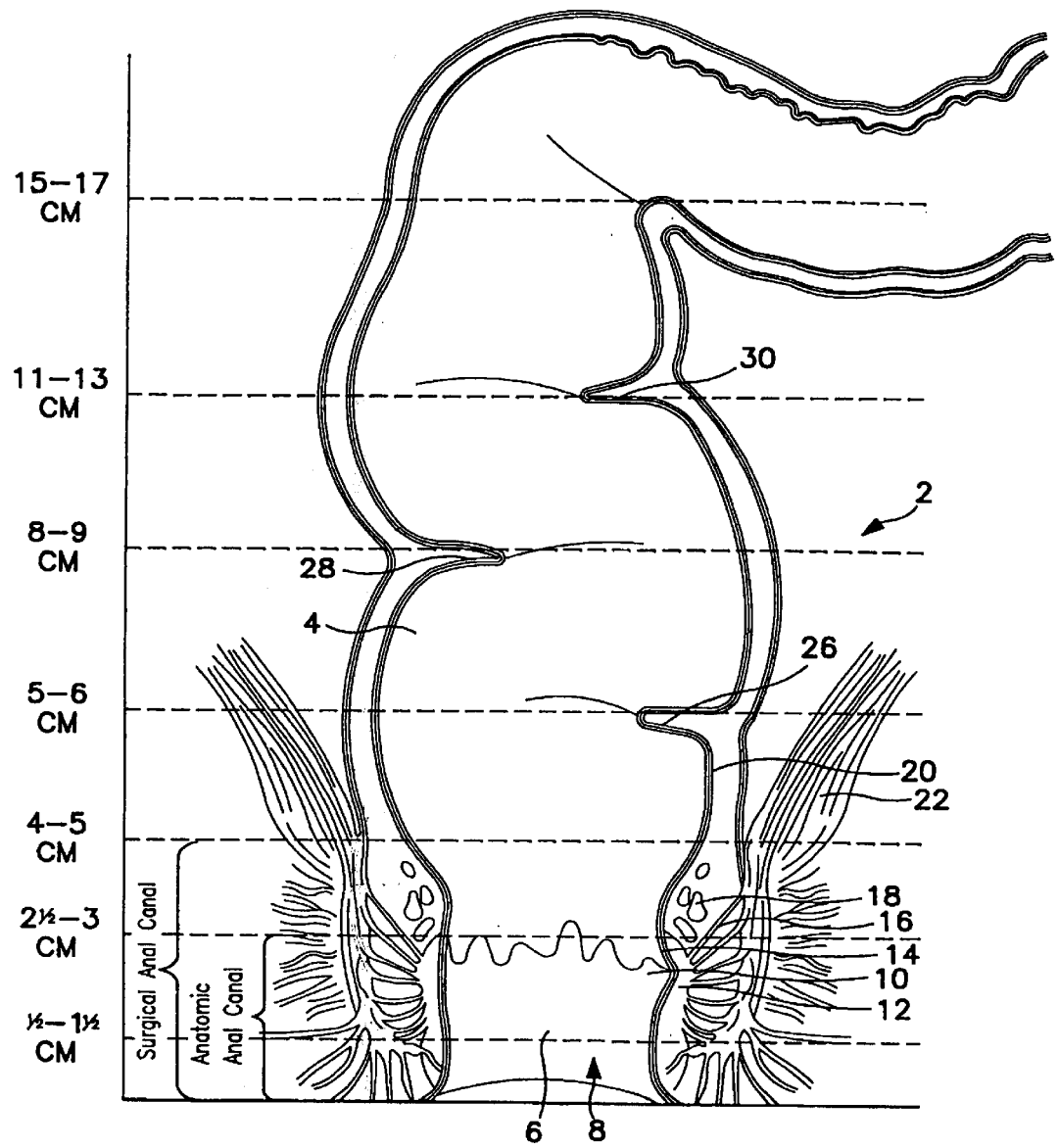
FIG. 1 is a cross-sectional side view of the human anal canal.
Figure 2:
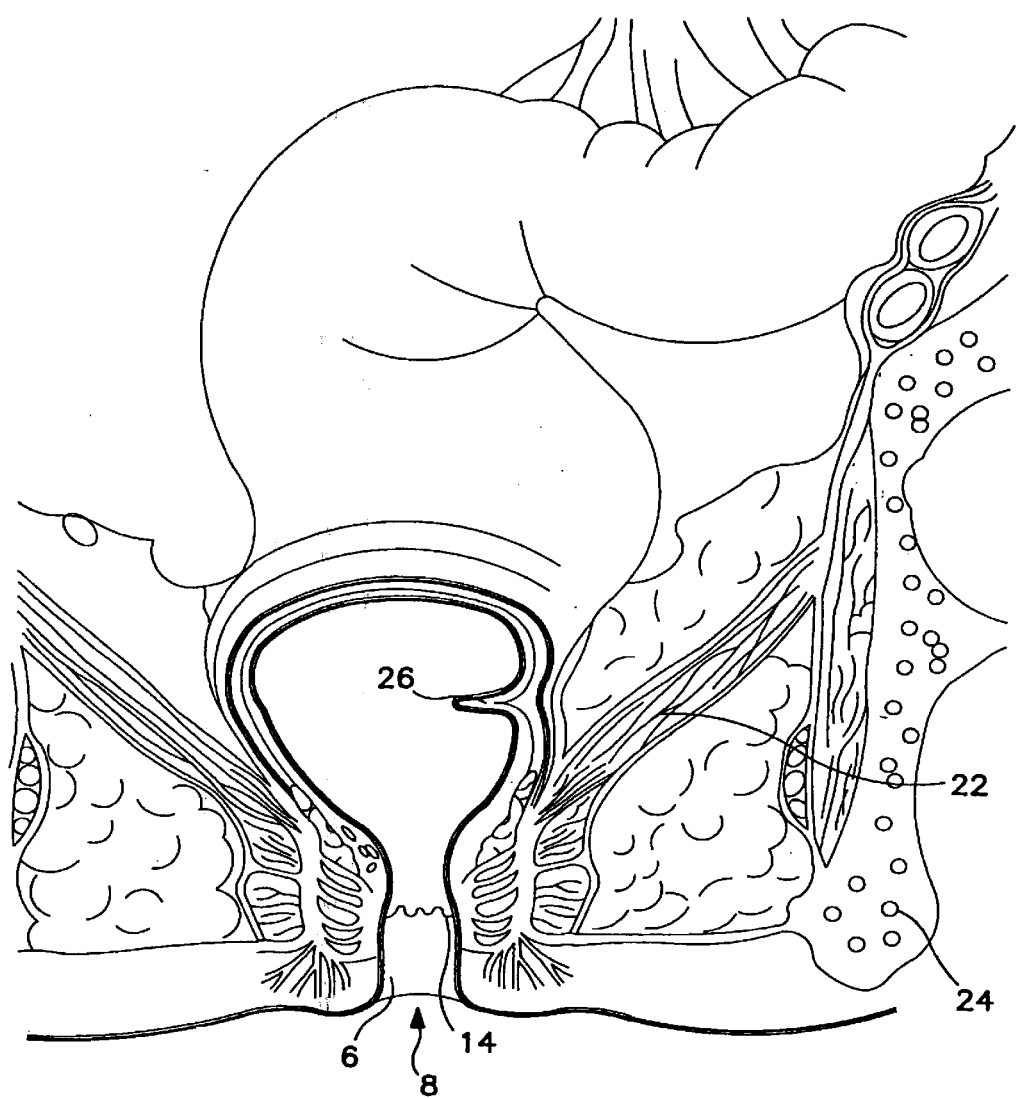
FIG. 2 is a bottom view of the pelvic floor.
Figure 3:
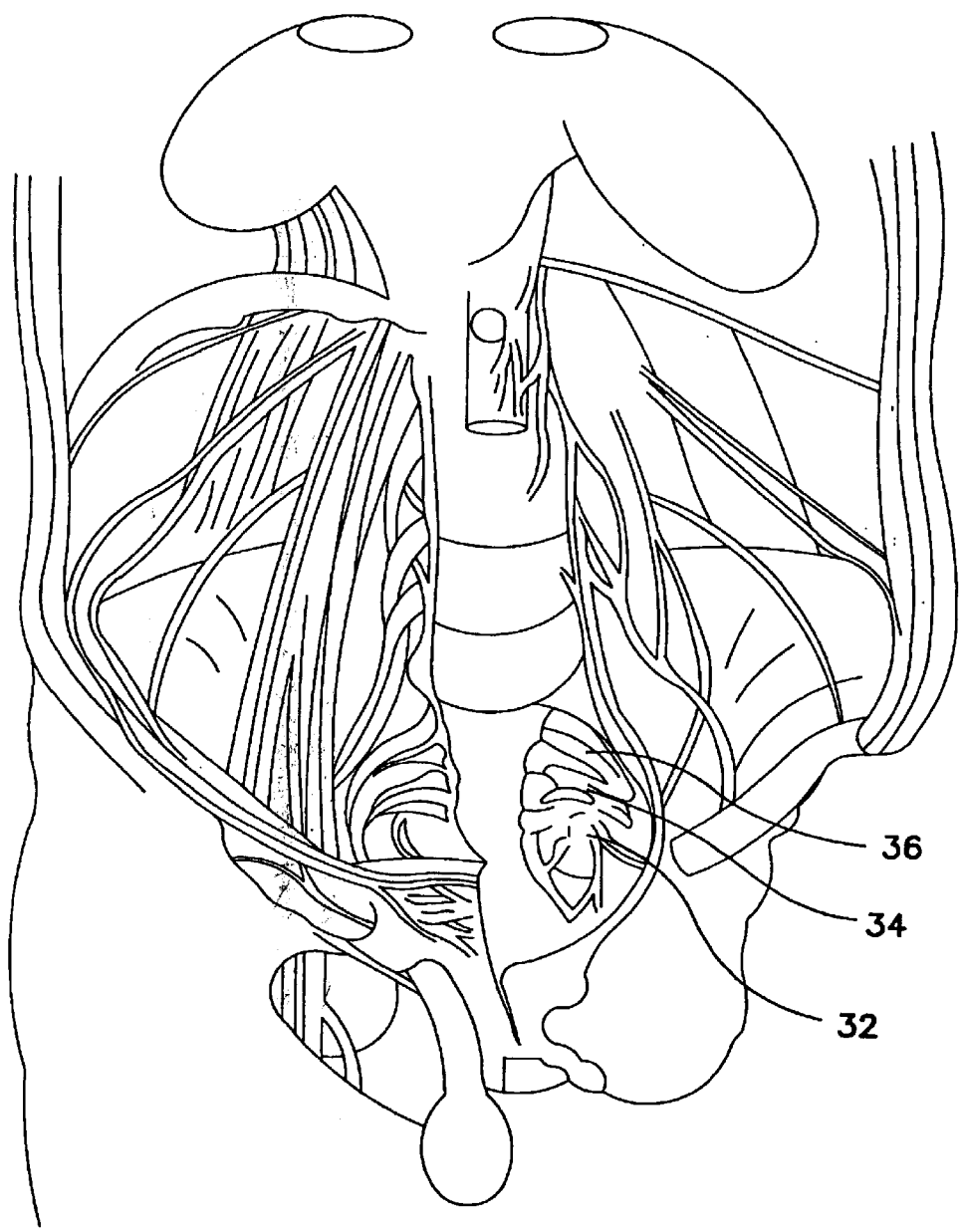
FIG. 3 is a cross-sectional side view of the innervation of the pelvic floor.

A recording probe according to the preferred embodiment of the invention is shown in FIGS. 4–9 generally labeled 38. Probe 38 has a distal end 40 and a proximal end 42. Distal end 40 terminates in an ultimate distal end 44. Probe 38 also has an elongated body 46 and a distensible sheath 48. Body 46 is elongated along an axis 50 and has an outer surface 52.

Sheath 48 surrounds the elongated body 46 at the distal end 40 of probe 38. Sheath 48 has an outside surface 54 and an inside surface 56. Sheath 48 preferably includes a first wing 58 and a second wing 60 that are attached to the body 46 proximal to the ultimate distal end 44 at 62. Sheath 48 is preferable made of a flexible material such as is well known in the art. Examples of this material include, but are not limited to, polyurethane, silicone or other silastic material. Other thermoplastics and polymers such as nylon, polytetrafluoroethylene or the like might also be adapted to such use. The particular material used in construction of sheath 48 itself is not important in the context of this invention so long as the material is a suitable biocompatible polymer that can function as an electrical insulator and provide sufficient support for electrodes as will be explained hereafter. Because sheath 48 is made of a flexible material, the distal end of sheath 48 may be moved away from axis 50 as will be described hereafter while the proximal end of first and second wings 58, 60 remains attached to body 46. First and second wings 58, 60 may be attached to body 46 by any means as will be clear to those skilled in the art including but not limited to medical grade adhesives, thermo-molding or ultrasonic welding.

In the embodiment shown in FIGS. 4–9, the distal end of outside surface 54 of sheath 48 has distal recording electrodes 64 attached to it. At least one distal recording electrode 64 is preferably attached near the distal end of each of the first and second wings 58, 60. Of course, only a single distal recording electrode 64 may be attached to the outside surface of either first or second wing 58, 60 if desired. In this embodiment, distal recording electrodes 64 may be relatively small, preferably about 1 mm or less in surface area. However, distal recording electrodes 64 may be larger or smaller as desired. Electrodes 64 are made of an electrically conductive material such as is well understood in the art such as platinum iridium, platinum, gold, silver, palladium, other noble metals and other alloys or metals suitable for use in the human body. Distal recording electrodes 64 are attached to sheath 48 by means well known in the art including but not limited to medical grade adhesives.

In the preferred embodiment of the invention, probe 38 also has proximal recording electrodes 66 attached to the outer surface 52 of body 46. At least one proximal recording electrode 66 is preferably attached to each side of body 46. As will be described in more detail hereafter in connection with the description of the use of the invention, proximal recording electrodes 66 should be located along the outer surface 52 of body 46 so that in use, proximal recording electrodes 66 will be located at or near the groove 14 in the anal canal 6.

In this embodiment, proximal recording electrodes 66 may also be relatively small, preferably about 1 mm or less in surface area. However, proximal recording electrodes 66 may be larger or smaller as desired. Proximal recording electrodes 66 are also attached to body 46 by means well known in the art including but not limited to medical grade adhesives.

Figure 10:
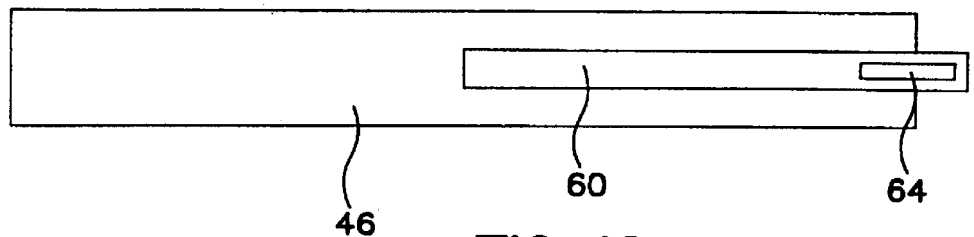
FIG. 10 is a side view of the device of FIG. 4 in a non-inflated form with an alternate configuration of electrodes.
Figure 11:
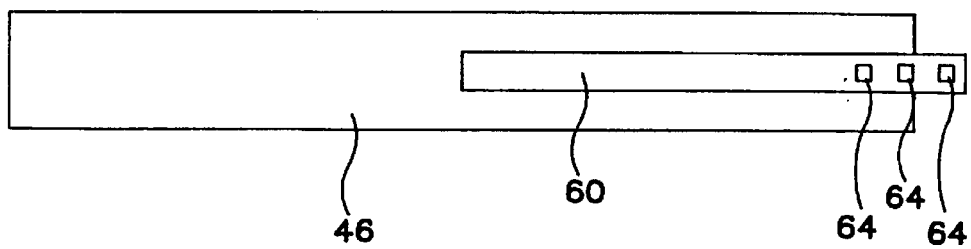
FIG. 11 is a side view of the device of FIG. 4 in a non-inflated form with an alternate configuration of electrodes.
Figure 12:
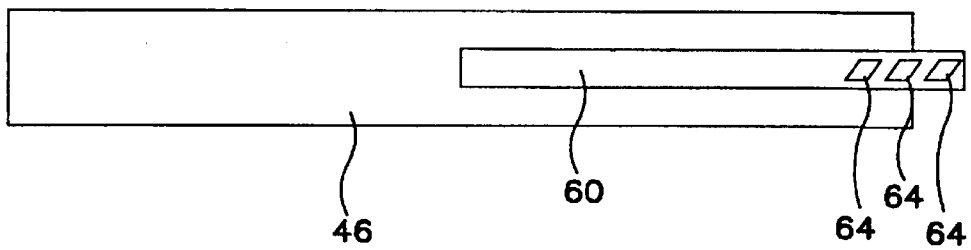
FIG. 12 is a side view of the device of FIG. 4 in a non-inflated form with an alternate configuration of electrodes.

In other embodiments as shown in FIGS. 10–12, distal recording electrodes 64 are elongated in a preferred direction. In the embodiment shown in FIG. 10, the distal recording electrodes 64 are elongated in a direction substantially parallel to the axis 50. In the embodiment shown in FIG. 11, the distal recording electrodes 64 are elongated in a direction substantially perpendicular to the axis 50. In a variant of the embodiments shown in FIGS. 10 and 11, the distal recording electrodes 64 may also have a configuration as shown in FIG. 12 where the distal recording electrodes 64 have both a significant elongated component in both the direction of and perpendicular to the axis 50.

In a similar fashion to the modification of distal recording electrodes 64, proximal recording electrodes 66 may be modified in shape. It is to be understood however, that the shape of distal recording electrodes 64 and proximal recording electrodes 66 may take whatever shape is desired, especially those described above, irrespective of the shape of the other.

Recording electrodes 64, or other recording electrodes as will be explained hereafter, should be located on the probe 38, in the whatever disclosed embodiment, so that the electrodes will be placed in contact with the tissue of interest. In particular, it is desirable to measure electrical activity in smooth muscle such as that found in the rectal or bladder wall and striated muscle of the pelvic floor. Striated muscle in the pelvic floor level has a deep level corresponding primarily to the levator ani muscles and a superficial level corresponding primarily to the external and urethral sphincters but also including ischeo cavemosal muscles, bulbal cavemosal muscles and transverse peroniteal muscles. In addition, recording electrodes preferably need to be placed off the physiologic midline to record electrical activity of the muscles on either side of the physiologic midline. Recording electrodes may be placed on the physiologic midline if desired. In view of the foregoing, the recording electrodes should be located on the probe 38, as will be clear to those skilled in the art, to sense electrical activity in the muscles described.

Further, it may be desirable to have only a single recording electrode or multiple recording electrodes. It is to be understood, however, that regardless of whether there is a single or multiple recording electrodes, there needs to be a neutral electrode so that a complete electrical current path is provided. The neutral electrode may be place on the probe itself or separately, for example, on the patient's skin.

A distending balloon 68, having an outer surface 70, is attached to body 46 within sheath 48. Distending balloon 68 is attached to the body 46 distal to the point of attachment of first and second wings 58, 60 at 62. At this location, the outer surface 70 of distending balloon 68 comes into contact with the inside surface 56 of sheath 48. Distending balloon 68 may be inflated as described below whereby distending balloon 68 increases in cross-sectional diameter. As distending balloon 68 increases in diameter, contact between inside surface 56 and outer surface 70 moves sheath 48 away from axis 50.

Distending balloon 68 is preferably made of a flexible elastomeric material such as urethane as is well understood in the art of catheter making, particularly as it relates to the manufacture of urinary catheters known as Foley catheters. Distending balloon 68 is connected to an inflation lumen 72 that runs through body 46.

Figure 4:
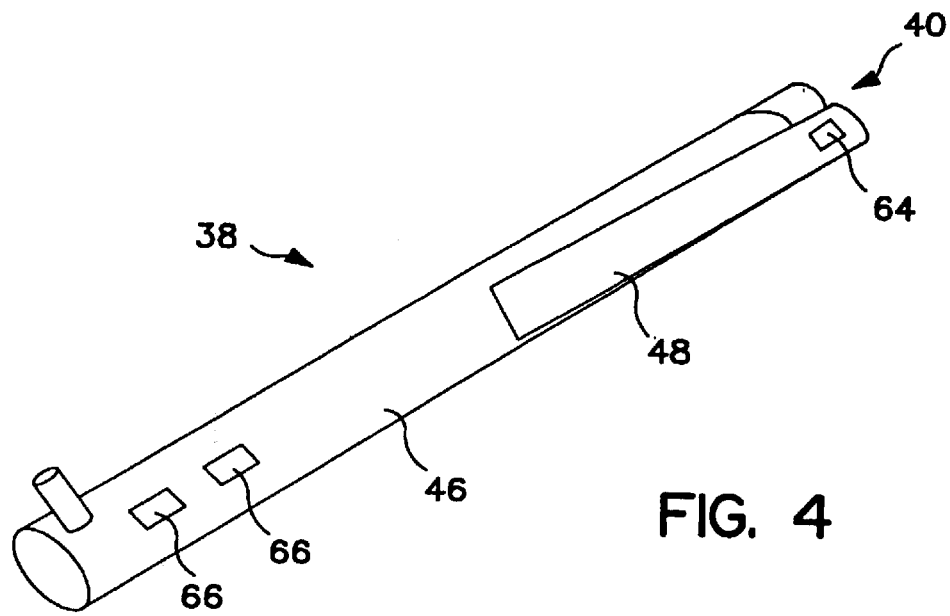
FIG. 4 is a perspective view of one embodiment of the probe of the present invention in a non-inflated form.
Figure 5:
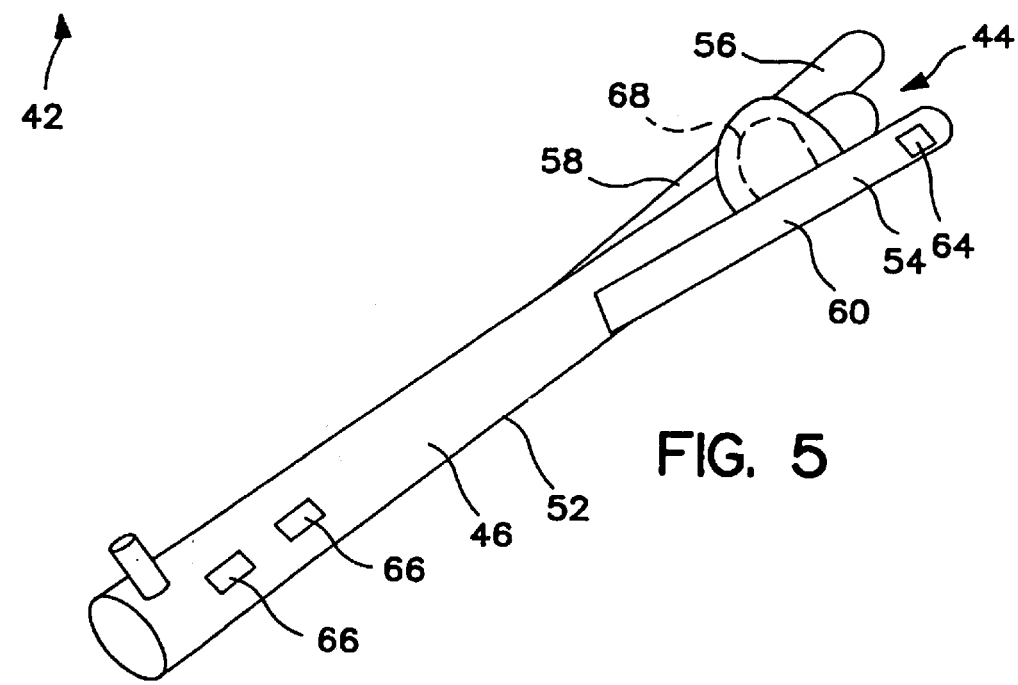
FIG. 5 is a perspective view of the embodiment of FIG. 4 in an inflated form.
Figure 6:
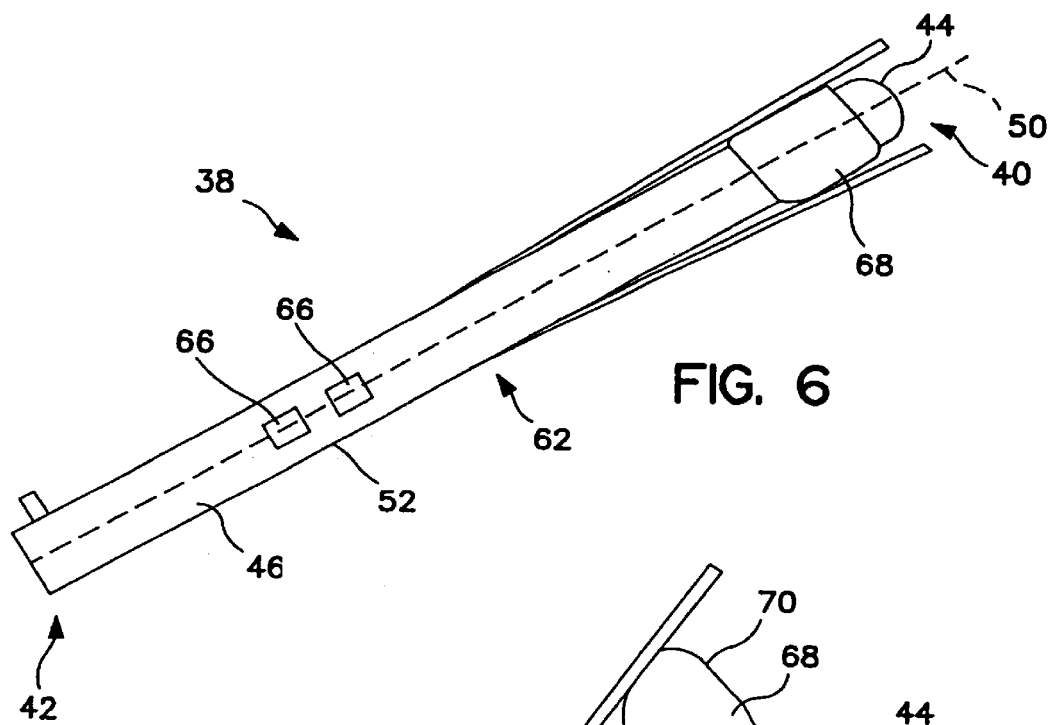
FIG. 6 is a top view of the embodiment of FIG. 4 in a non-inflated form.
Figure 7:
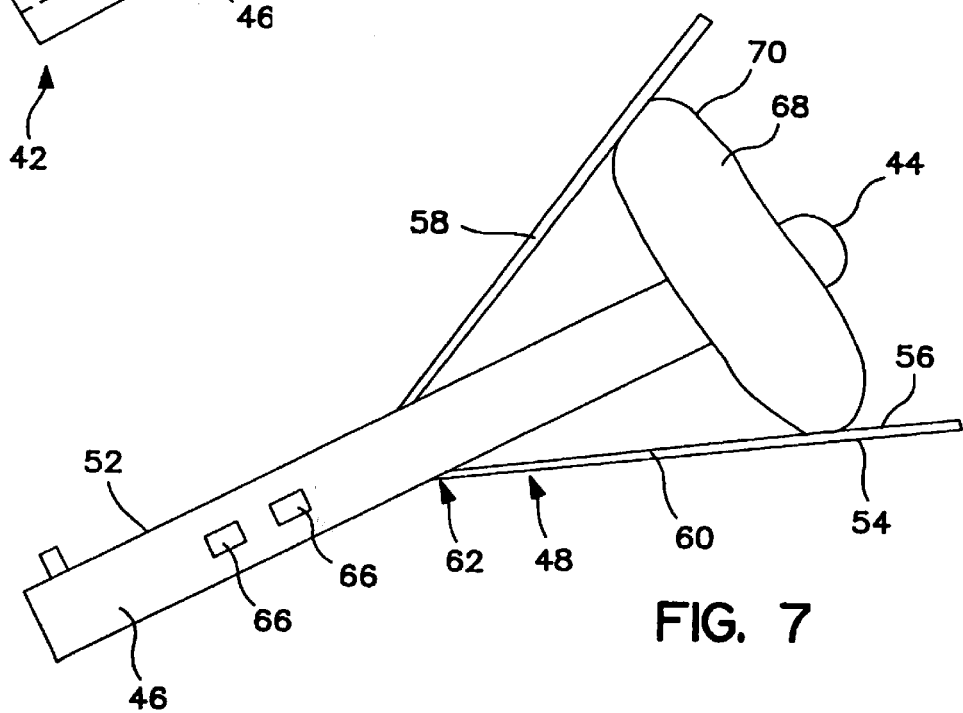
FIG. 7 is a top view of the embodiment of FIG. 4 in an inflated form.
Figure 8:
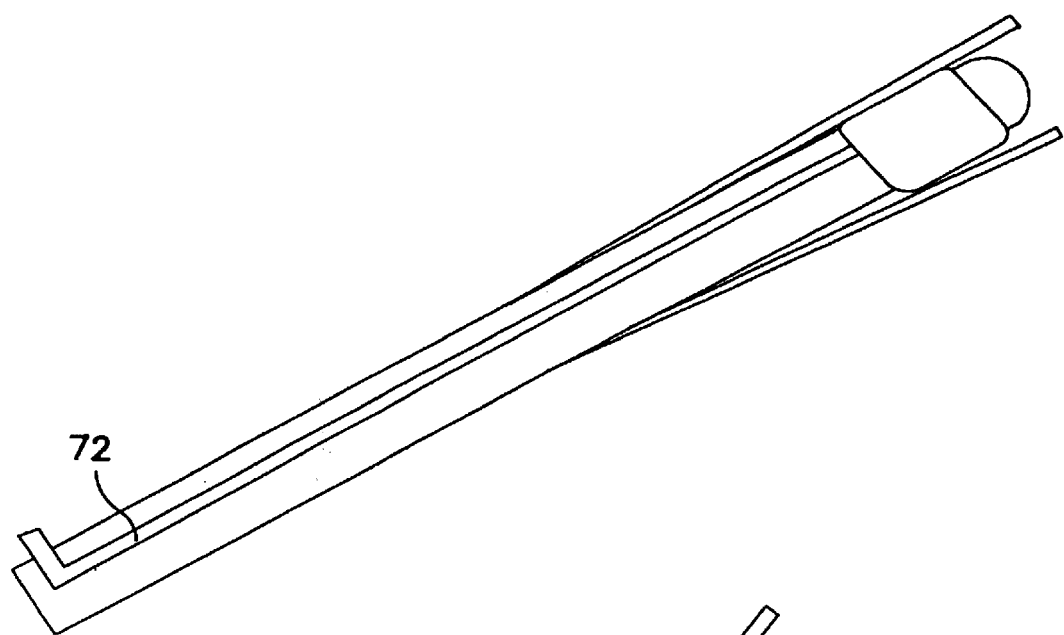
FIG. 8 is a top cross-sectional view of the embodiment of FIG. 4 in a non-inflated form.
Figure 9:
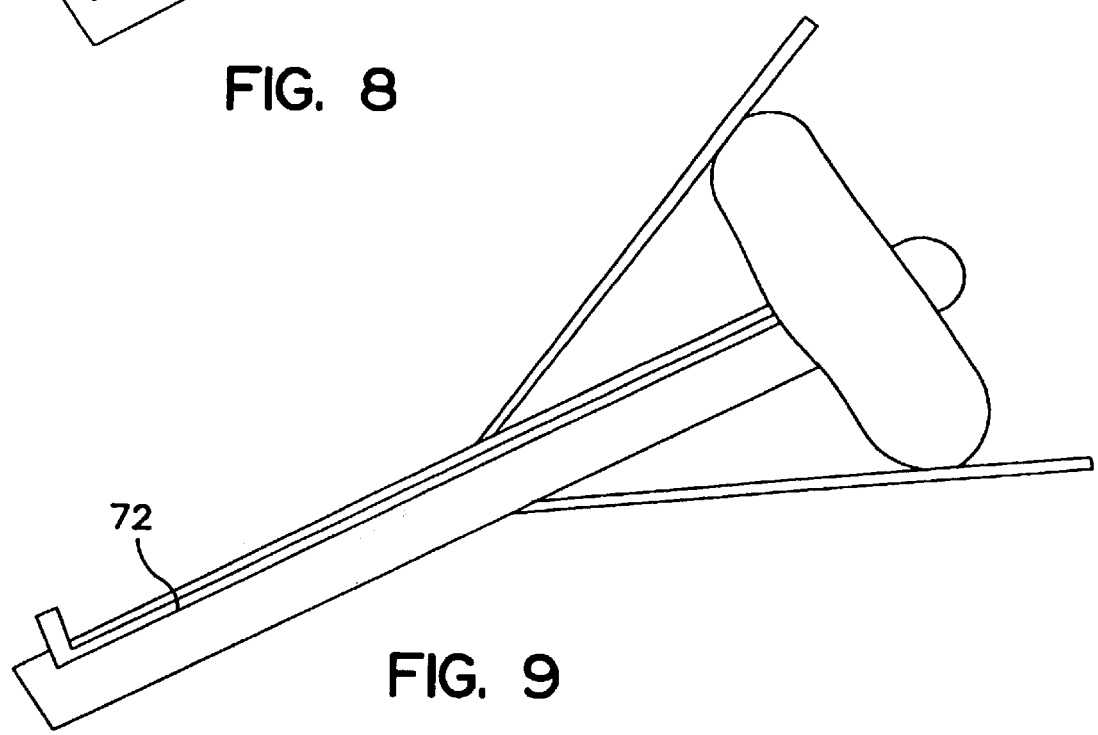
FIG. 9 is a top cross-sectional view of the embodiment of FIG. 4 in an inflated form.

FIGS. 4, 6 and 8 show the preferred embodiment of the invention with the distending balloon 68 in a non-inflated form. However, distending balloon 68 may be inflated through inflation lumen 72 with a gas or liquid such as air or water as is well understood in the art. FIGS. 5, 7 and 9 show the preferred embodiment of the invention with the distending balloon 68 in an inflated form. Distending balloon 68 should preferably have a shape, when inflated, that allows distending balloon 68 to expand roughly perpendicular to axis 50 to move first and second wings 58, 60 away from axis 50. As a result, distending balloon 68 when inflated is preferably perfectly spherical having a volume, preferably, of between 20–30 cc. Alternately, distending balloon 68 may be elongated in a direction roughly perpendicular to axis 50. In either embodiment, distending balloon 68 needs to have dimensions, when inflated, push distending balloon 68 firmly against the rectal wall.

Figure 13:
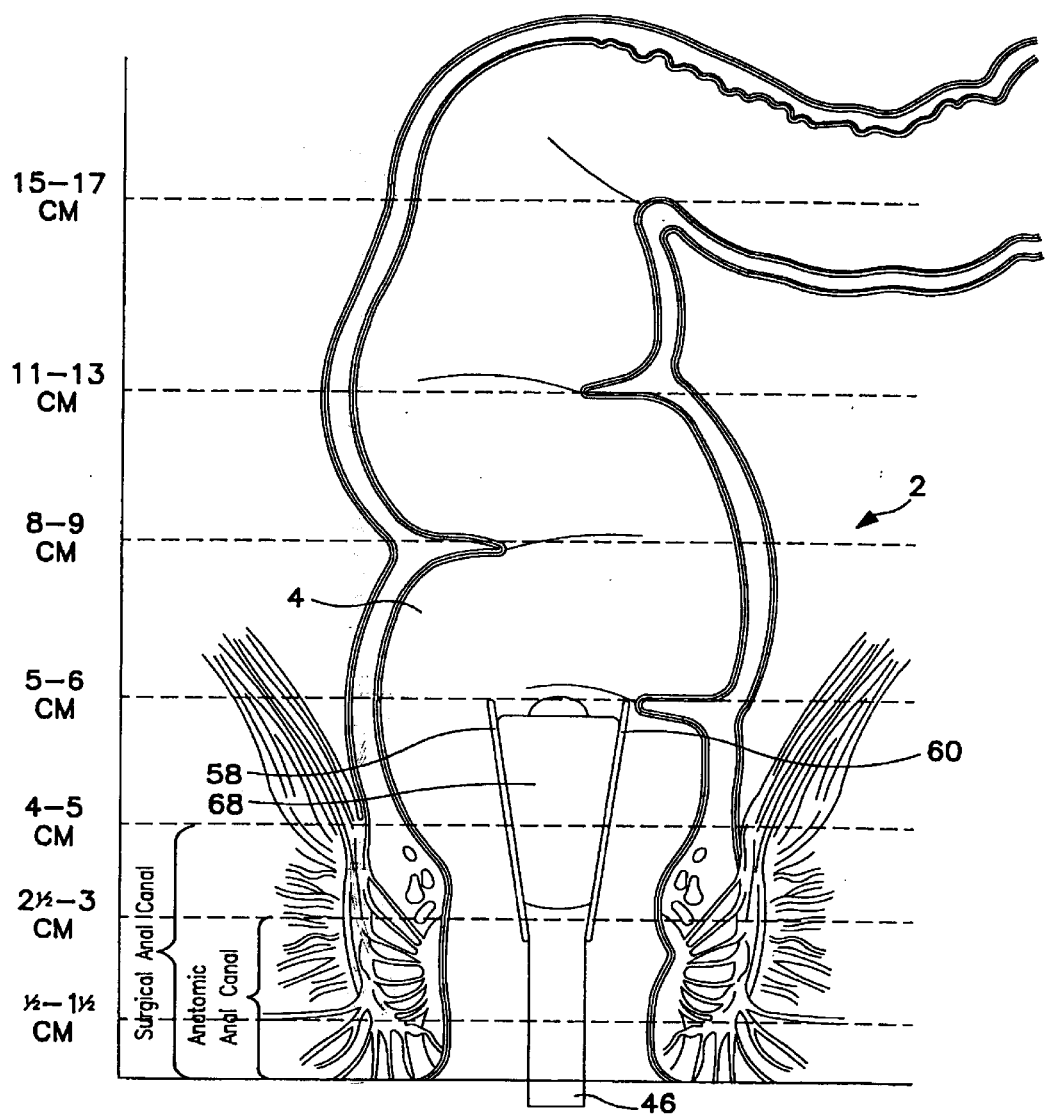
FIG. 13 is a sectional view of the device of FIG. 4 in a non-inflated form in place in a rectum.

As stated above, distending balloon 68 may be inflated through inflation lumen 72 with either a gas or liquid. In use, probe 38 is inserted into the anal canal 6 so that the distal end 40 of probe 38 extends past the point of contact between the levator ani muscles 22 and the anal canal 6 (FIG. 13). In particular, the probe 38 is inserted into the anal canal 6 a sufficient distance so that distending balloon 68 and the distal end of first and second wings 58, 60 extend past the levator ani muscles 22.

Figure 14:
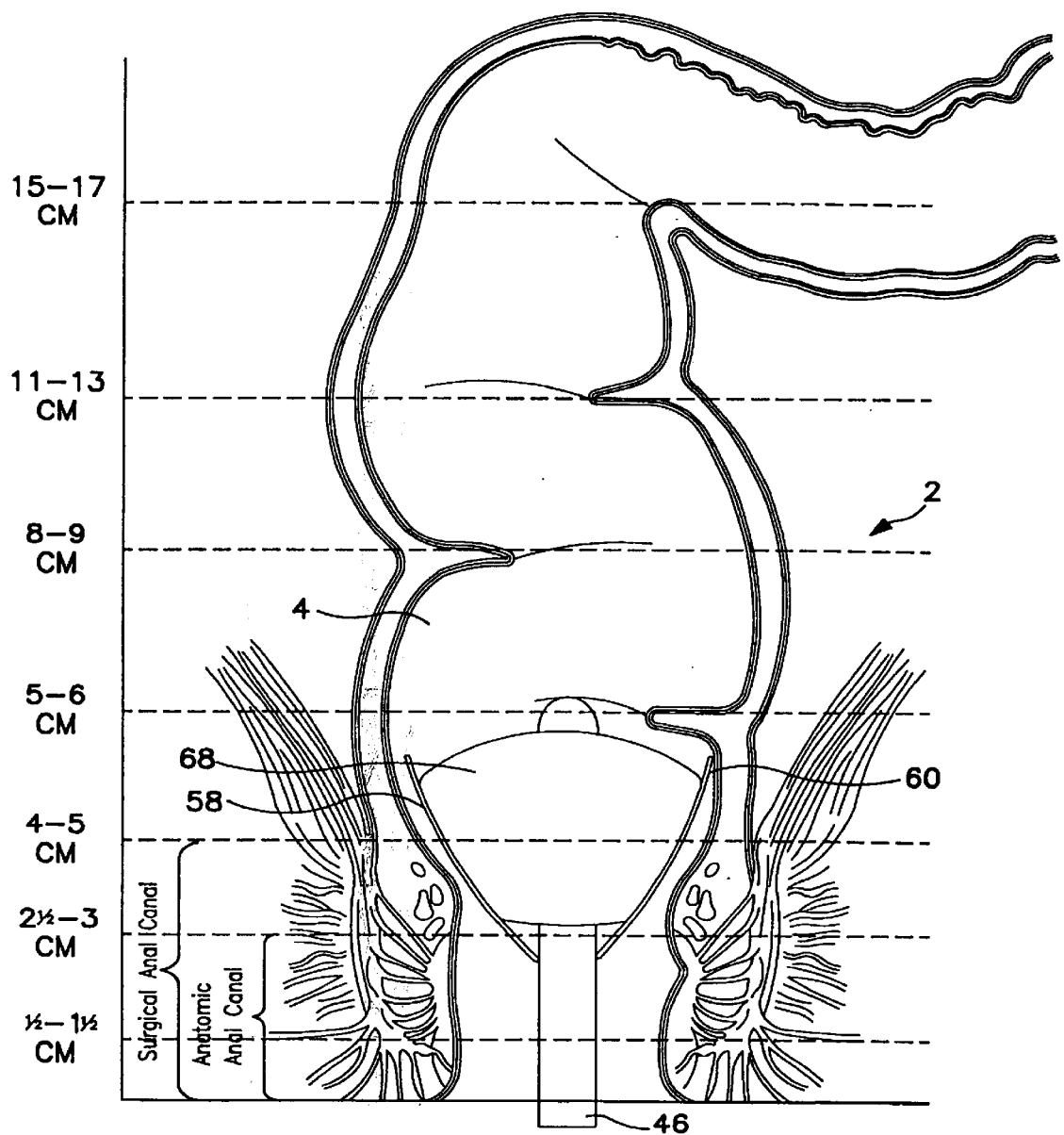
FIG. 14 is a sectional view of the device of FIG. 4 in an inflated form in place in a rectum.

The distending balloon 68 is inflated. As distending balloon 68 inflates, distal recording electrodes 64 are moved into contact with the tissue inside the rectum 4, near the levator ani muscles 22, at a slight pressure (FIG. 14). There, recording electrodes 64 will be able to detect electrical activity due to afferent and efferent nerve impulses in the pelvic floor.

Further, proximal recording electrodes 66 will be in contact with the tissue of the anal canal 6 at about the area of the groove 14 near the anal crypt 12. There, proximal recording electrodes 66 will be able to detect electrical activity due to afferent and efferent nerve impulses in the pelvic floor at a slightly different perspective than will be detected by distal recording electrodes 64. The difference in electrical activity detected by distal recording electrodes 64 and proximal recording electrodes 66 may be diagnostically significant.

Figure 15:
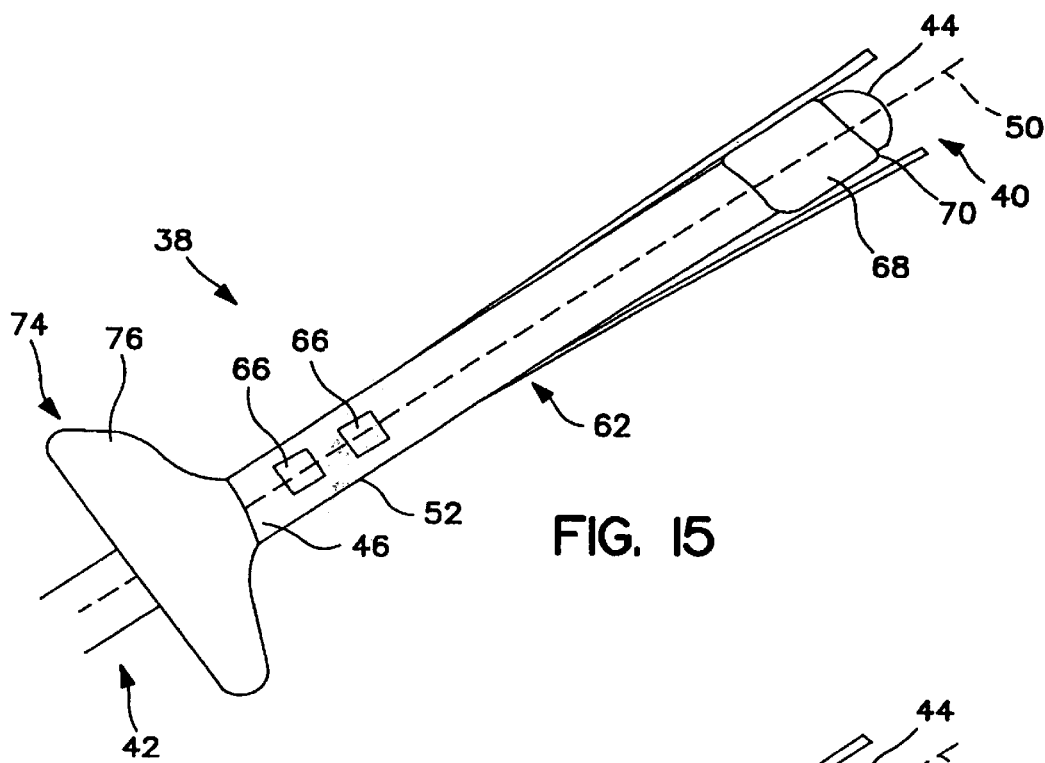
FIG. 15 is a top view of an alternate embodiment of the invention of FIG. 4.
Figure 16:
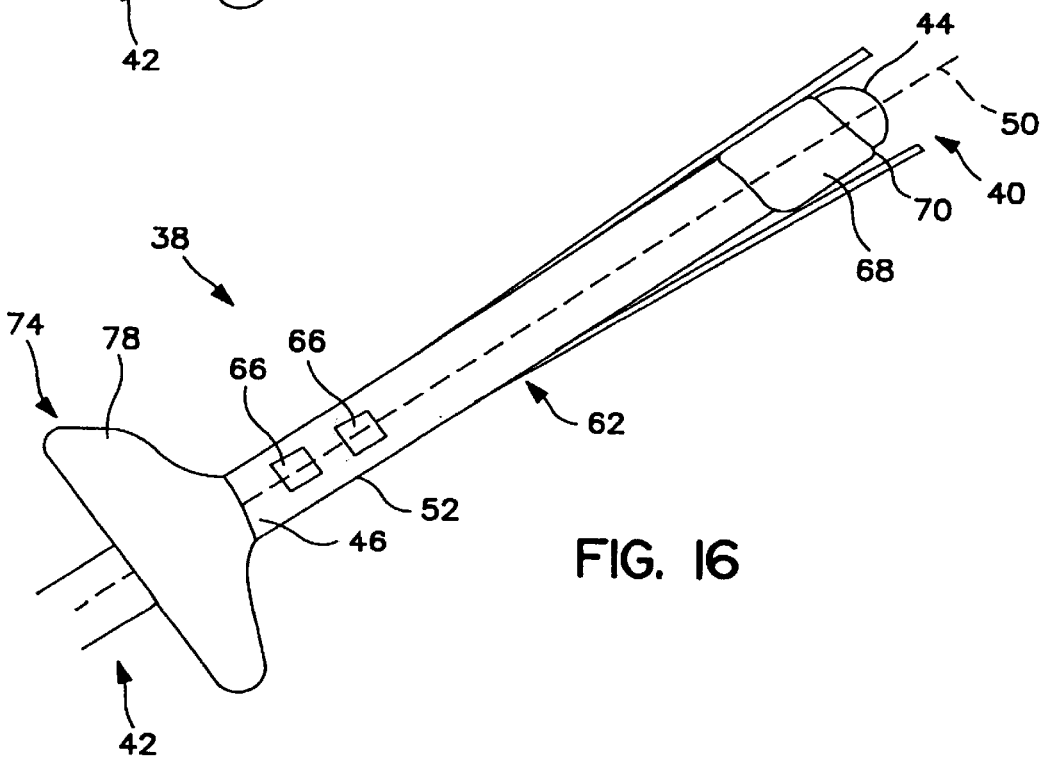
FIG. 16 is a top view of an alternate embodiment of the invention of FIG. 4.

Additionally, as shown in an alternate embodiment in FIGS. 15–16, it may be desirable to have a locating structure 74 located near the proximal end 42 of probe 38 to aid in securely locating probe 38.

In the embodiment of FIG. 15, locating structure 74 may take the form of a movable ring 76 that has the general shape of a doughnut. Movable ring 76 is movable proximally and distally along the outer surface 70 of body 46. Movable ring 76 may be made of a relatively hard, resilient plastic foam such as silicone rubber or a closed cell foam, to name a few possibilities that will be clear to those skilled in the art. Movable ring 76 has an inner diameter sized to allow it to be in frictional contact with the outer surface 70 of body 46. Movable ring 76 is then moved proximally or distally along the outer surface 70 of body 46 by sliding movable ring 76 from a first position to the new desired position. It may be useful for movable ring 76 to have a shape that conforms to the external configuration of the anal canal 6.

In another embodiment shown in FIG. 16, locating structure 74 may take the form of an external locating balloon 78. External locating balloon 78 is preferably made similarly to distending balloon 68. An inflation lumen 80 inflates external locating balloon 78. It may be useful for external locating balloon 78 to have a shape that conforms to the external configuration of the anal canal 6.

Figure 17:
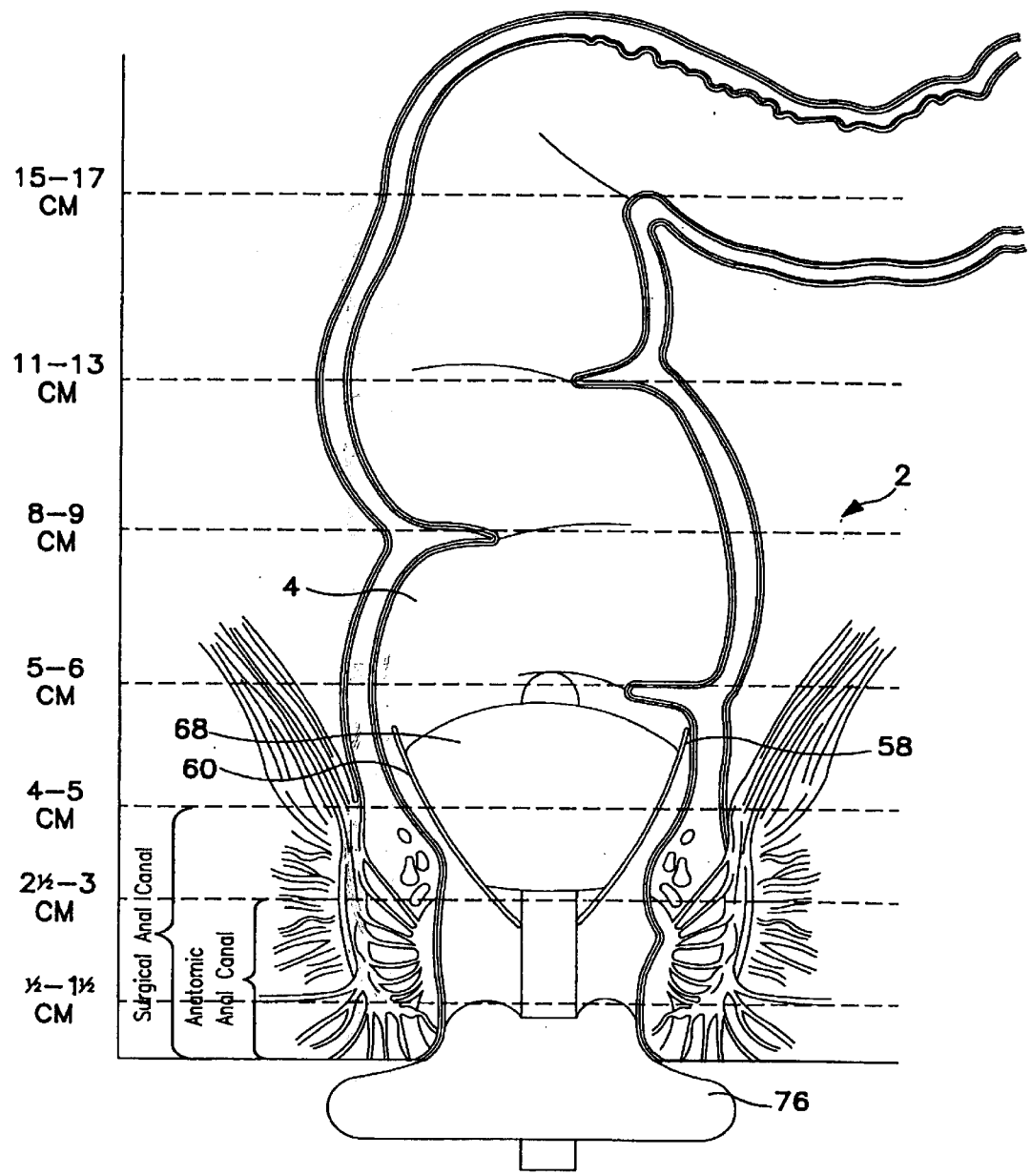
FIG. 17 is a sectional view of the embodiment of FIG. 15 in place in an anal canal.
Figure 18:
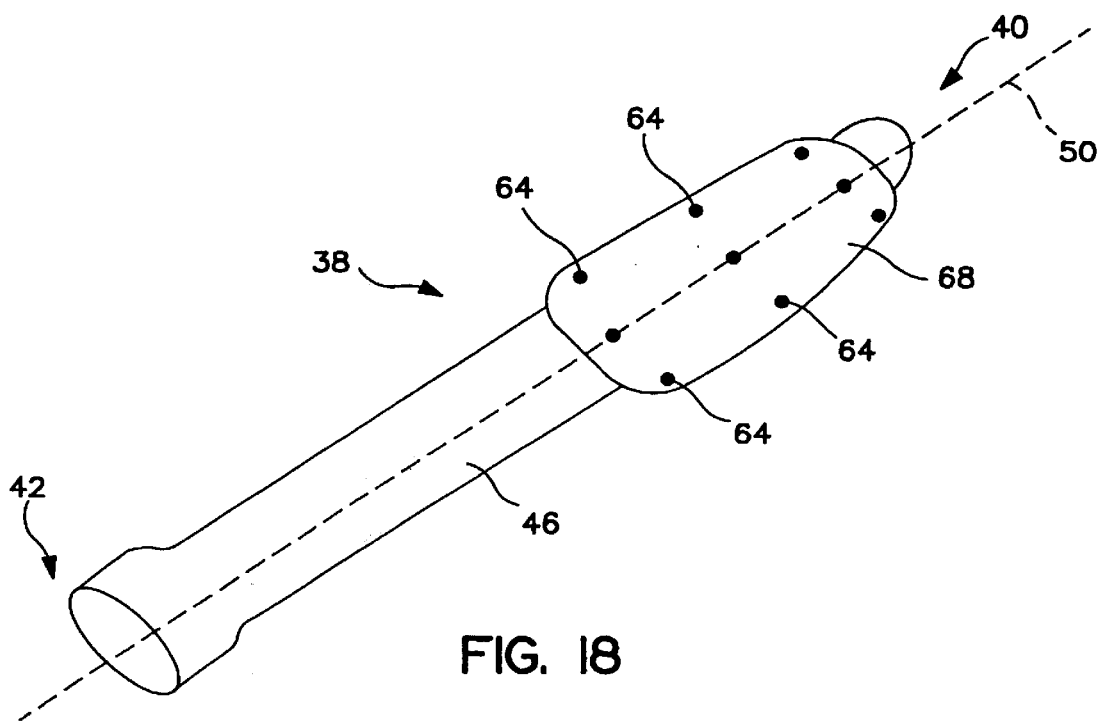
FIG. 18 is a perspective view of an alternate embodiment of the probe of the present invention in a non-inflated form.
Figure 19:
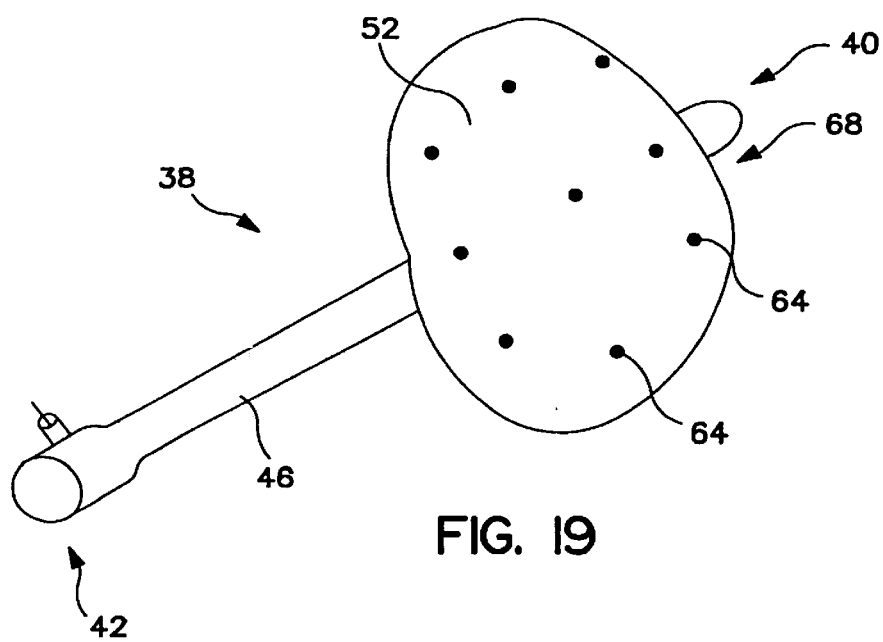
FIG. 19 is a perspective view of the embodiment of FIG. 18 in an inflated form.
Figure 20:
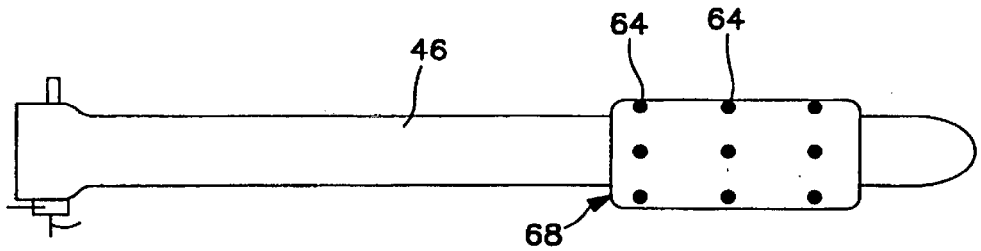
FIG. 20 is a side view of the embodiment of FIG. 18 in a non-inflated form.
Figure 21:
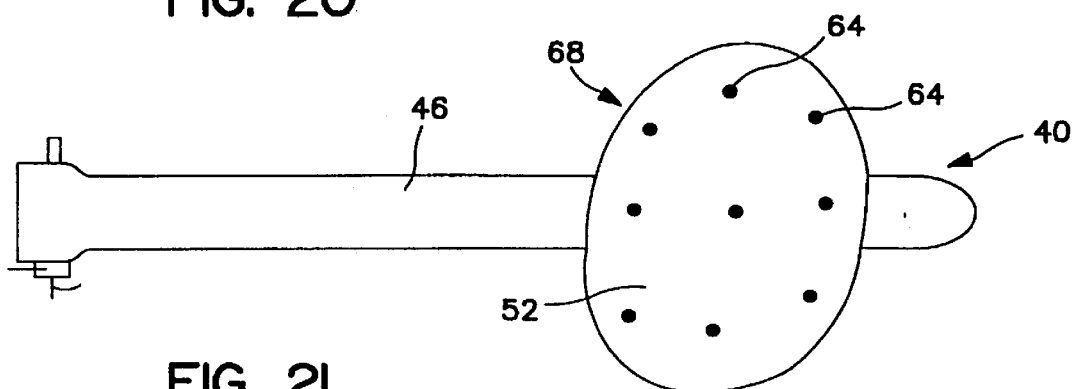
FIG. 21 is a side view of the embodiment of FIG. 18 in an inflated form.
Figure 22:
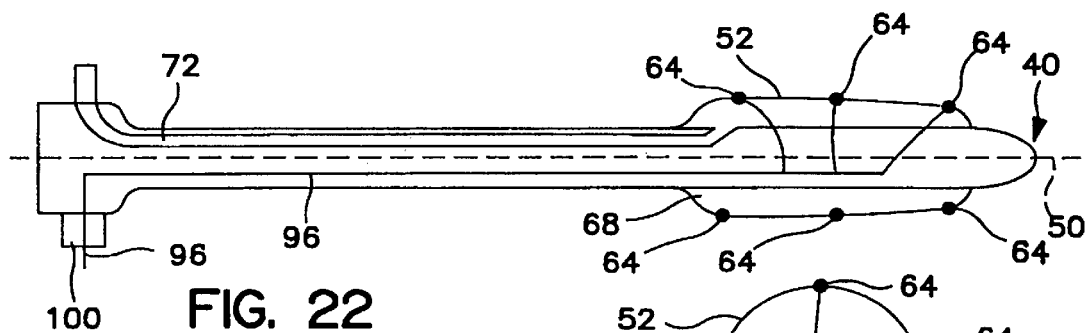
FIG. 22 is a side cross-sectional view of the embodiment of FIG. 18 in a non-inflated form.
Figure 23:
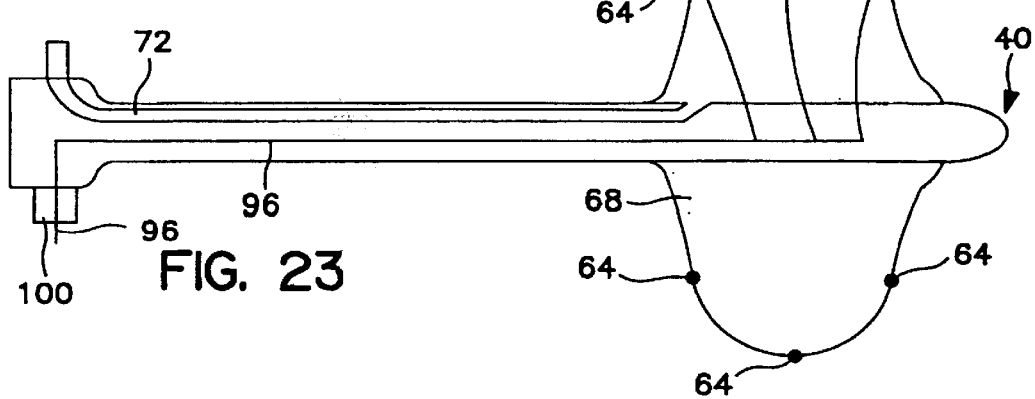
FIG. 23 is a side cross-sectional view of the embodiment of FIG. 18 in an inflated form.
Figure 24:
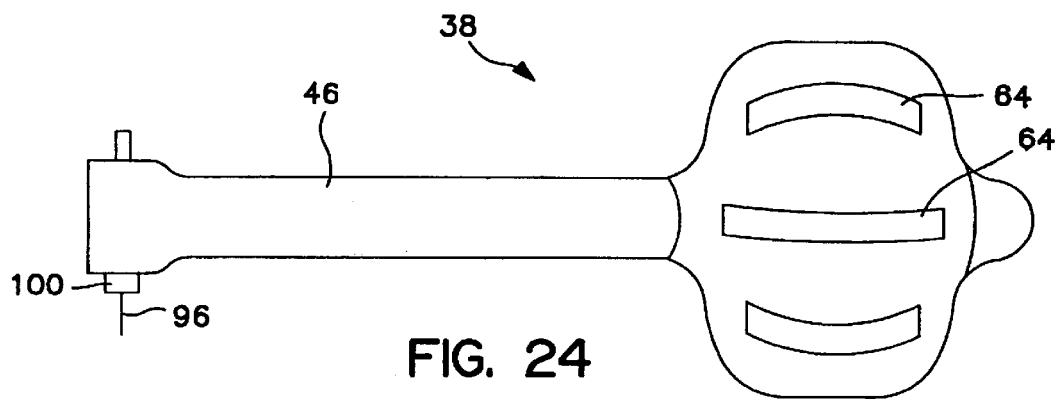
FIG. 24 is a side view of the device of FIG. 18 in an inflated form with an alternate configuration of electrodes.
Figure 25:
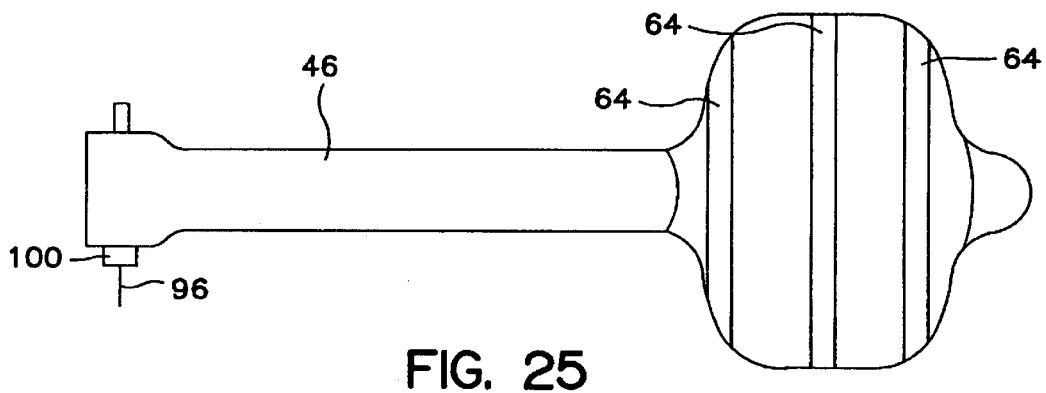
FIG. 25 is a side view of the device of FIG. 18 in an inflated form with an alternate configuration of electrodes.

In use, sheath 48 and distending balloon 68 is placed on the inside of the rectum 4 with either movable ring 76 or external locating balloon 78 located outside the rectum against the sphincter 16. FIG. 17 shows the embodiment of FIG. 15 in position in anal canal 6. In this configuration, the anal sphincter 16 will be located between sheath 48 and the distending balloon 68 and either the movable ring 76 or the external locating balloon 78. The interaction between external locating balloon 78 and the inflated distending balloon 68 with the tissue of the anal canal 6 will hold the probe 38 in a fixed and desired position.

An alternate embodiment of the invention is shown in FIGS. 18–29. In this embodiment, there is no sheath 48. Instead, distal recording electrodes 64 are attached directly to the outer surface 70 of distending balloon 68.

In the embodiment shown in FIGS. 18–23, the outer surface 70 of distending balloon 68 has a series of distal recording electrodes 64 attached to it. In this embodiment, distal recording electrodes 64 may again be relatively small, preferably about 1 mm or less in surface area However, as above, distal recording electrodes 64 may be larger or smaller as desired. Distal recording electrodes 64 are attached to inflation balloon 68 by means well known in the art including but not limited to medical grade adhesives.

Figure 26:
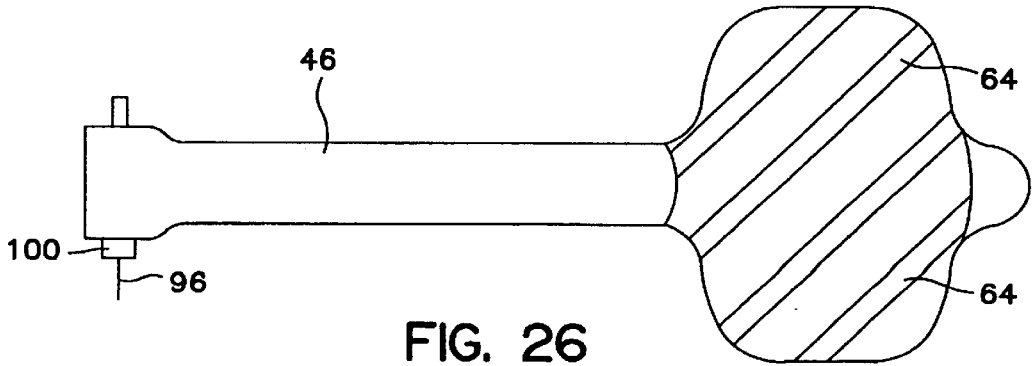
FIG. 26 is a side view of the device of FIG. 18 in an inflated form with an alternate configuration of electrodes.
Figure 27:
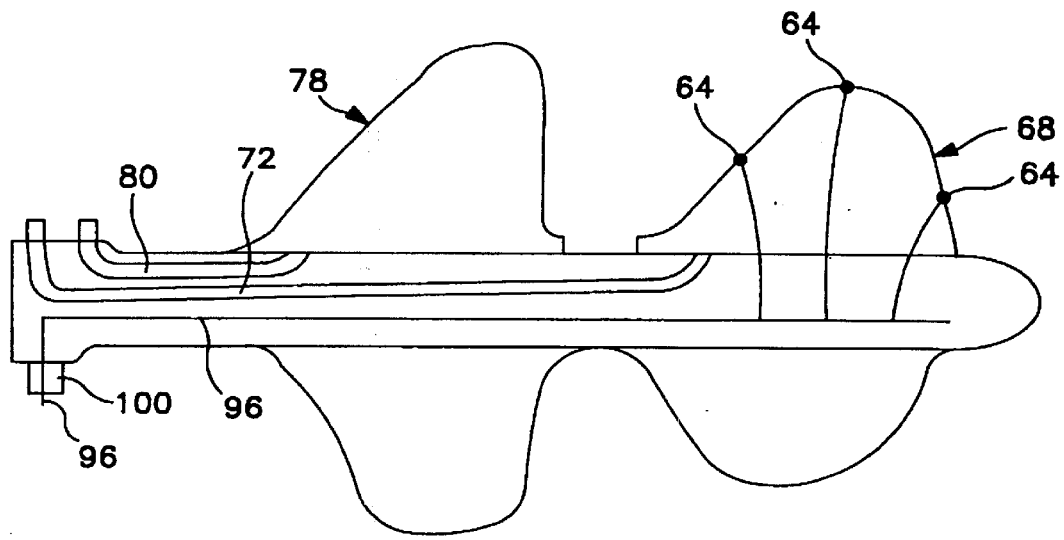
FIG. 27 is a side cross-sectional view of an alternate embodiment of the invention of FIG. 18.

In other embodiments as shown in FIGS. 24–29, distal recording electrodes 64 are elongated in a preferred direction. In the embodiment shown in FIG. 24, the distal recording electrodes 64 are elongated in a direction substantially parallel to the axis 50. In the embodiment shown in FIG. 25, the distal recording electrodes 64 are elongated in a direction substantially perpendicular to the axis 50. In a variant of the embodiments shown in FIGS. 24 and 25, the distal recording electrodes 64 may also have a configuration as shown in FIG. 26 where the distal recording electrodes 64 have both a significant elongated component in both the direction of and perpendicular to the axis 50.

As stated above, distending balloon 68 may be inflated through inflation lumen 72 with either a gas or liquid. As distending balloon 68 inflates, distal recording electrodes 64 are moved into contact with the tissue inside the rectum 4 at a slight pressure. There, distal recording electrodes 64 will be able to detect electrical activity due to afferent and efferent nerve impulses in the pelvic floor.

In this embodiment as well, it may be desirable to have proximal recording electrodes 66 located along body 46 as described above. Additionally, as shown in an alternate embodiment in FIG. 27, it may be desirable to have a locating structure 74 as described above.

Figure 28:
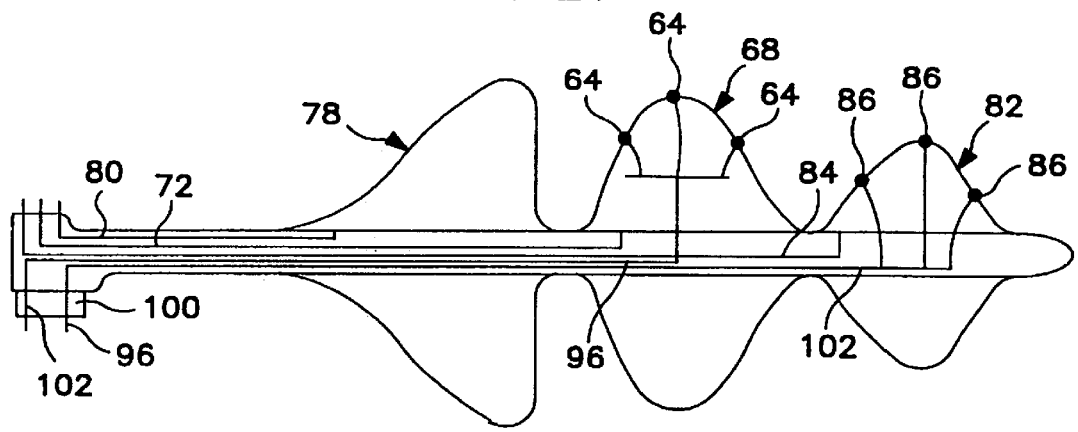
FIG. 28 is a side cross-sectional view of an alternate embodiment of the invention of FIG. 18.

It may be desirable to add one or more additional inflation balloons to the probe 38 to detect nerve electrical activity at more than one place in the rectum 4. For example, FIG. 28 shows the addition of a second inflation balloon 82 distal to inflation balloon 68. A second inflation lumen 84 inflates second inflation balloon 82 in a similar fashion as inflation lumen 72 inflates inflation balloon 68. A series of second distal recording electrodes 86 are attached to second inflation balloon 82 in similar arrangement and fashion as distal recording electrodes 64 are attached to inflation balloon 68.

Figure 29:
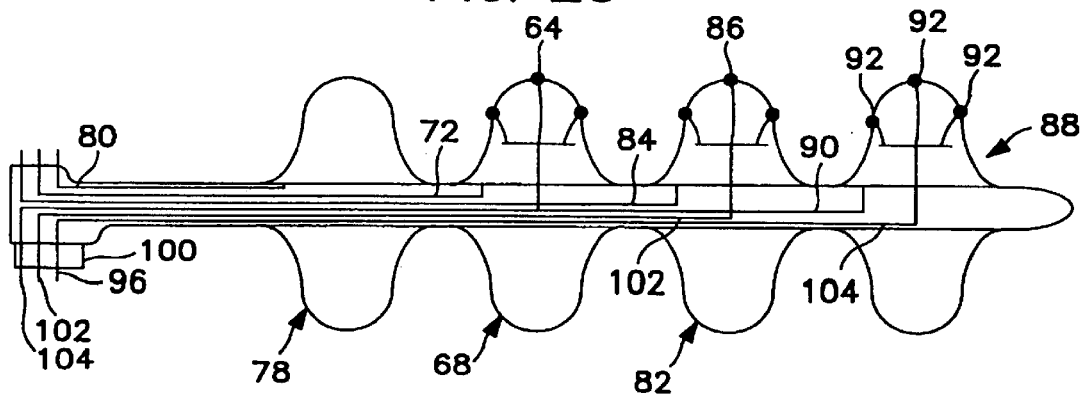
FIG. 29 is a side cross-sectional view of an alternate embodiment of the invention of FIG. 18.
Figure 30:
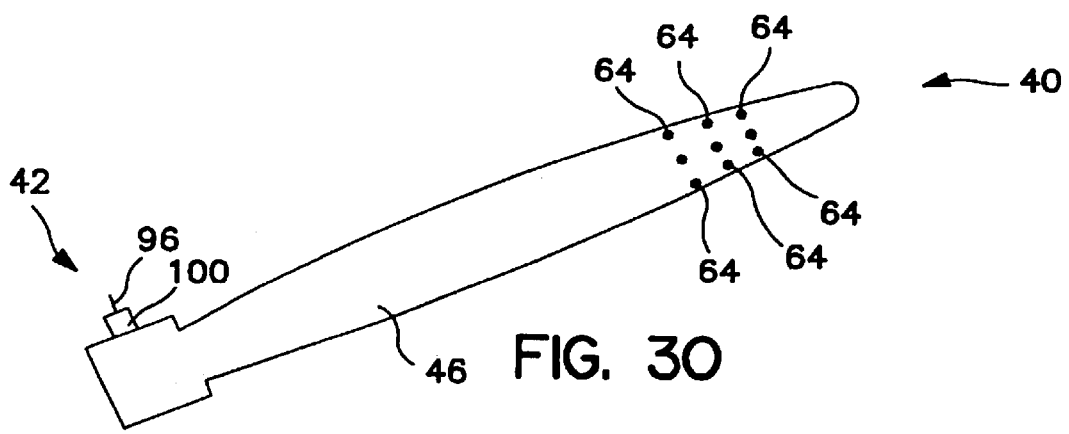
FIG. 30 is a perspective view of an alternate embodiment of the invention.
Figure 31:
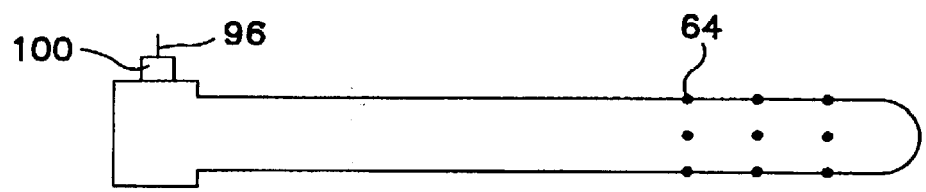
FIG. 31 is a side view of the embodiment of FIG. 30.
Figure 32:
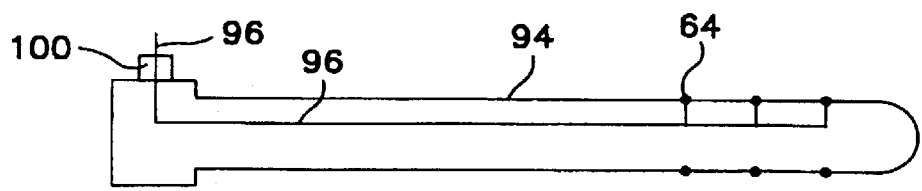
FIG. 32 is a side cross-sectional view of the embodiment of FIG. 30.
Figure 33:
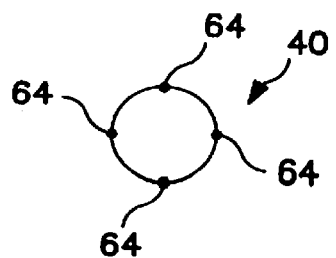
FIG. 33 is an end view of the embodiment of FIG. 30.

In a further embodiment shown in FIG. 29, a third inflation balloon 88 is added to probe 38 distal to second inflation balloon 82. A third inflation lumen 90 inflates third inflation balloon 88 in a similar fashion as inflation lumen 72 and second inflation lumen 84 inflates inflation balloon 68 and second inflation balloon 82, respectively. A series of third distal recording electrodes 92 are attached to third inflation balloon 88 in similar arrangement and fashion as distal recording electrodes 64 and second distal recording electrodes 86 are attached to inflation balloon 68 and second inflation balloon 82, respectively.

In either the embodiment of FIGS. 28 or 29, the second distal recording electrodes 86 and the third distal recording electrodes 92 may have the same configuration as distal recording electrodes 64 or may have different configurations as desired. Further, second distal recording electrodes 86 and third distal recording electrodes 92 may have the same or different configurations with each other as desired. In the embodiments of the invention described above, the distal recording electrodes 86 and 92 are attached to their respective inflation balloons 82, 88 in a similar manner as are distal recording electrodes 64 attached to distending balloon 68. Further, these embodiments may or may not have a locating structure 74 as desired.

Figure 34:
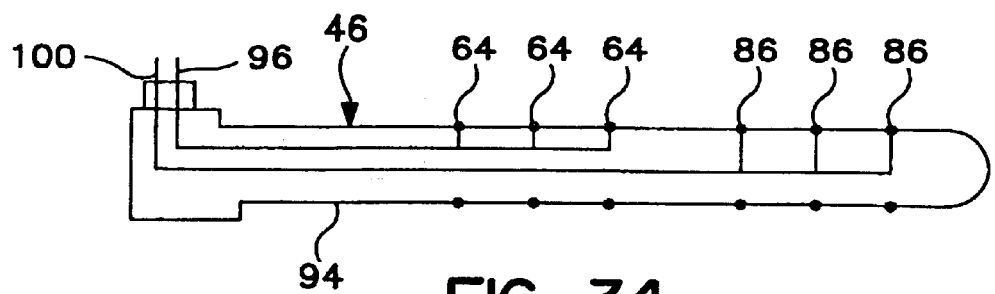
FIG. 34 is a side view of an alternate embodiment of the invention shown in FIG. 30.
Figure 35:
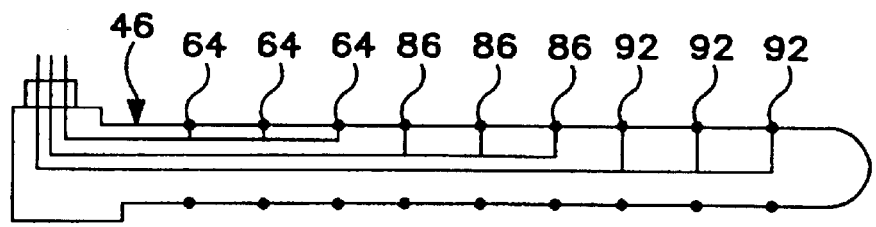
FIG. 35 is a side view of an alternate embodiment of the invention shown in FIG. 30.

In another embodiment shown in FIGS. 30–35, distal recording electrodes 64 may be attached directly to the outside of the distal end 40 of the body 46. In this embodiment, there is no distending balloon 68 or inflation balloons 82, 88. In this embodiment, there may or may not be an external locating structure 74 as desired. However, instead of having distal recording electrodes 64 attached to the distending balloon 68, body 46 itself has a series of distal recording electrodes 64 attached to its outer surface 94. In this embodiment, distal recording electrodes 64 are located on the outer surface 94 of body 46 so that the distal recording electrodes 64 cannot move relative to the outer surface 94 of body 46. It may be desirable to add a series of electrodes such as a set of second distal recording electrodes 86 or third distal recording electrodes 92 as is shown in FIGS. 34 and 35, respectively.

In all of the embodiments shown above, distal recording electrodes 64 and proximal recording electrodes 66, if present, are attached through wires 96, 98, respectively, to a connector 100 located at the proximal end 42. In the embodiments having additional sets of distal recording electrodes, 86, 92, additional wires 102, 104, respectively, connect distal recording electrodes, 86, 92, to connector 100. Wires 96, 98, 102, and 104 may either run along the outer or inner surface of body 46 or may be embedded in the material of body 46 through processes well understood in the art, including but not limited to, co-extruding wires 96, 98, 102 and 104 with the material of body 46. Connector 100 allows the distal recording electrodes 64, 86, or 92 and proximal recording electrodes 66 of probe 38 to be connected to a control device 106 to process and display the electrical signals detected by distal recording electrodes 64, 86 or 92 and proximal recording electrodes 66.

Figure 36:
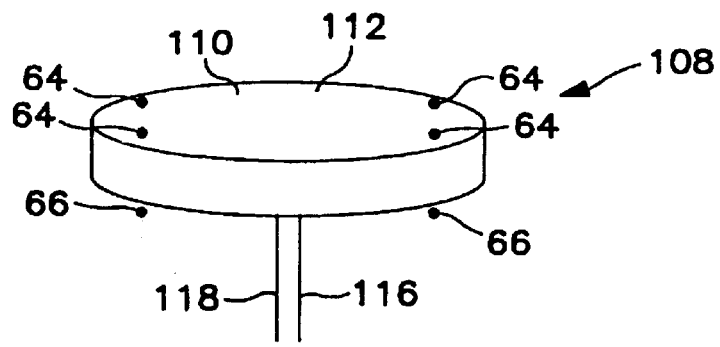
FIG. 36 is a perspective view of an alternate embodiment of the invention.
Figure 37:
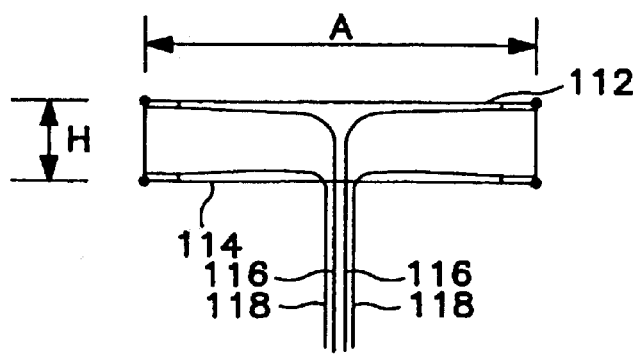
FIG. 37 is a side cross-sectional view of the embodiment shown in FIG. 36.

In another alternate embodiment of the invention shown in FIGS. 36–37, probe 38 is a disk 108. Disk 108 has a disk body 110, distal recording electrodes 64 and proximal recording electrodes 66. Disk body 110 is preferable disk shaped and made of a flexible material such as a relatively stiff foam rubber like silicone rubber or a closed cell foam, to name a few possibilities that will be clear to those skilled in the art. Disk body 110 has a width "A", a height "H", an upper surface 112 and a lower surface 114. Disk body 110 should have a dimension across width "A" that would allow it to be placed in contact with the tissue of the anal canal 6 in the groove 14 of the anal canal 6 between the levator ani muscles 22 and the sphincter 16 near the anal crypt 12. Width "A" is preferably between about 1 cm. and 3 cm. recognizing that other dimensions may be necessary owing to the variability in anatomy from person to person. Further, it is clear that an embodiment adapted to pediatric use would probably require dimensions on the small end or even generally smaller than those listed above. It may be desirable to have an expandable disk 108 that allows various widths to be set. The key to the width "A" is that the disk 108 is snuggly and securely seated in groove 14 despite the various differences in individual body dimensions.

Likewise, height "H" is preferably between about 0.25 cm. and 0.5 cm. again allowing for greater or lesser dimensions according to varying anatomical measures and for pediatric use. Height "H" should not be so large as to move distal or proximal recording electrodes 64, 66 out of position next to the tissue of interest.

In the preferred embodiment, both distal recording electrodes 64 and proximal recording electrodes 66 are present. However, it is to be understood that either distal recording electrodes 64 or proximal recording electrodes 66 may be used independently without the other. Distal recording electrodes 64 are placed on the upper surface 112 while proximal recording electrodes 66 are placed on the lower surface 114. It is to understood, however, that either distal recording electrodes 64 or proximal recording electrodes 66 may be placed on the side of disk 108 between upper and lower surfaces 12, 114.

Distal and proximal recording electrodes 64, 66 may be attached to upper and lower surfaces 112, 114, respectively, through means similar to that described above for connecting distal recording electrodes 64 to the outer surface 70 of distending balloon 68 including but not limited to medical grade adhesives. Wires 116 and 118 are attached to distal and proximal recording electrodes 64, 66, respectively, and connect distal and proximal recording electrodes 64, 66 to connector 100 in similar fashion to wires 96 and 98.

Figure 38:
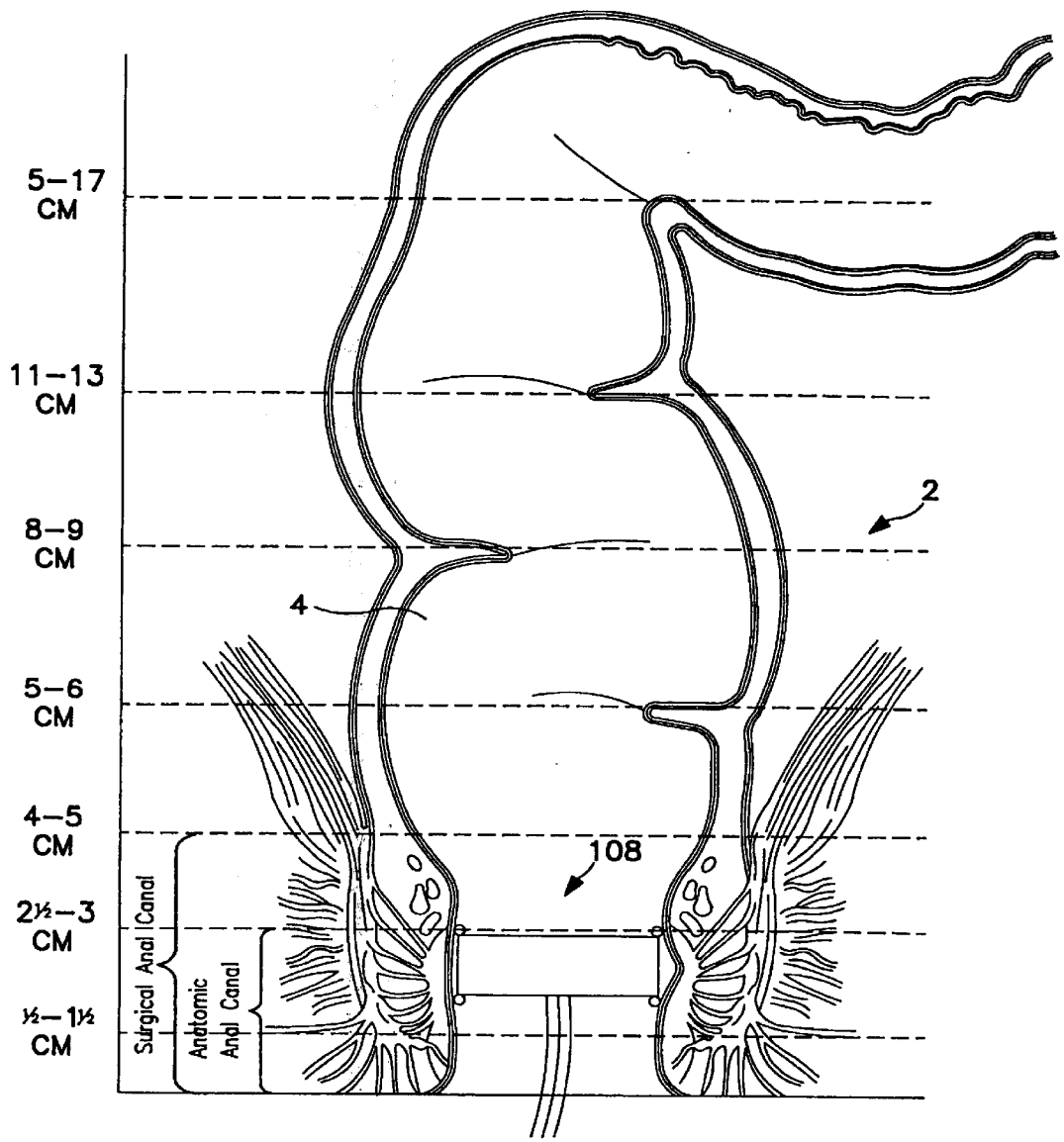
FIG. 38 is a sectional view of the embodiment of FIG. 36 in place in an anal canal.

In use, disk 108 is manually placed in the anal canal 6. Disk 108 is preferably located at about the groove 14 (FIG. 38).

Figure 39:
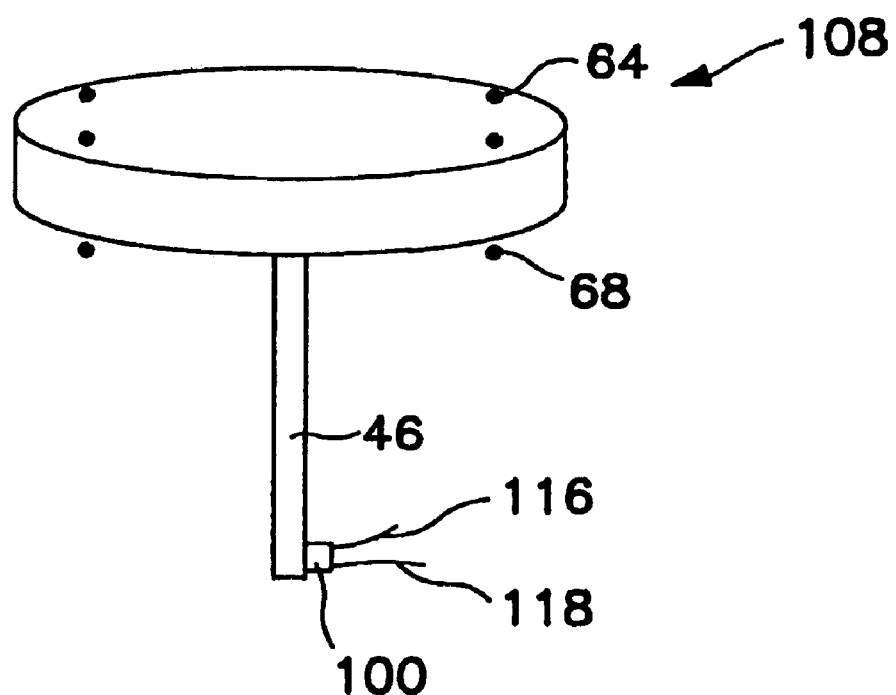
FIG. 39 shows a perspective view of an alternate embodiment of the invention of FIG. 36.

In a variant of the embodiment described immediately above and as shown in FIG. 39, disk 108 may be attached to a body 46 that allows disk 108 to be placed in the desired location in the anal canal 6 without the need to manually place the disk 108 in the desired location. In this embodiment, all features of disk 108 described above are retained. However, instead of being unsupported, wires 116 and 118 may either run along the outer or inner surface of body 46 or may be embedded in the material of body 46 through processes well understood in the art, including but not limited to, co-extruding wires 116 and 118 with the material of body 46.

In use in all the embodiments described, the distal recording electrodes 64, 86 or 92 and proximal recording electrodes 66 detect electrical energy from efferent and afferent nerve signals transmitted along nerves passing through or beginning or ending in tissue near the distal or proximal recording electrodes 64, 86, 92 or 66. Throughout this description, unless specifically stated otherwise, reference to distal recording electrodes 64 also refers to distal recording electrodes 52, 86 or 92. Further, unless specifically stated otherwise, reference to distal recording electrodes 64 also refers to proximal recording electrodes 66.

Distal recording electrodes 64 need to be able to sense electrical activity in the pelvic region typically of about 1–100 microvolts. Control device 106 contains an amplifier/filter 120 that processes the signal detected by distal recording electrodes 64 to indicate the electrical activity of the nerves in the pelvic floor.

Figure 40:
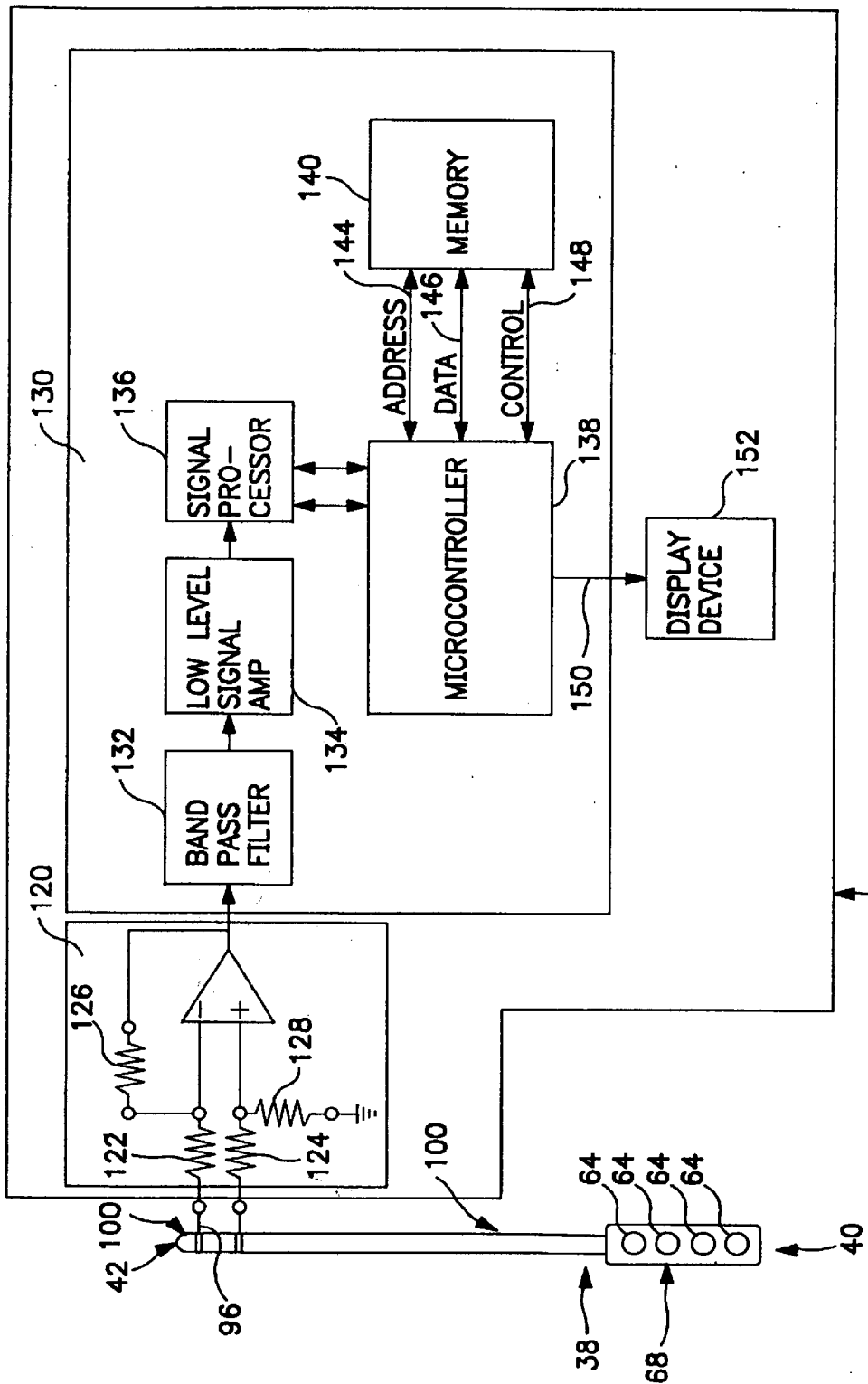
FIG. 40 is a schematic diagram showing an embodiment of the control device of the present invention.

As mentioned above and referring to FIG. 40, distal recording electrodes 64 are connected to amplifier/filter 120. Preferably, amplifier/filter 120 includes a conventional differential amplifier comprising an operational amplifier 94 and resistors 122, 124, 126 and 128 connected as shown. Wires 96 connect electrodes 64 to resistors 122 and 124. In embodiments having additional proximal recording electrodes 52, 86 or 92 or proximal recording electrodes 66, structure similar to amplifier/filter 120 and resistors 122, 124, 126 and 128 for each set of electrodes 52, 86, 92 or 66 will be present as will be clear to those skilled in the art.

The output of amplifier/filter 120 in one embodiment is connected to a controller 130 that further processes the amplified and filtered electrical activity detected by distal recording electrodes 64. In the embodiment shown in FIG. 40, controller 130 comprising a band pass filter 132, a low level signal amplifier 158, a signal processor 136, a microcontroller 138 and a memory 140. More specifically, signal processor 136 may take the form of a digital signal microprocessor, or, alternatively, an analog to digital converter. The output of signal processor 136 is conducted over a bus 142 to microcontroller 138. Microcontroller 138 communicates with memory 140 over an address bus 144, a data bus 146 and a control bus 148.

An output port of microcontroller 138 produces a signal on an output bus 150 that indicates the electrical activity detected by distal recording electrodes 64. Output bus 150 may be connected to a display device 152 that graphically indicates the electrical activity detected by distal recording electrodes 64. Display device 152 may be a display screen such as a video monitor or LCD screen, a printer or any other means for displaying visual information as will be well understood in the art. Alternately, output bus 150 may be connected to a means for audibly indicating the electrical activity detected by distal recording electrodes 64.

Figure 41:
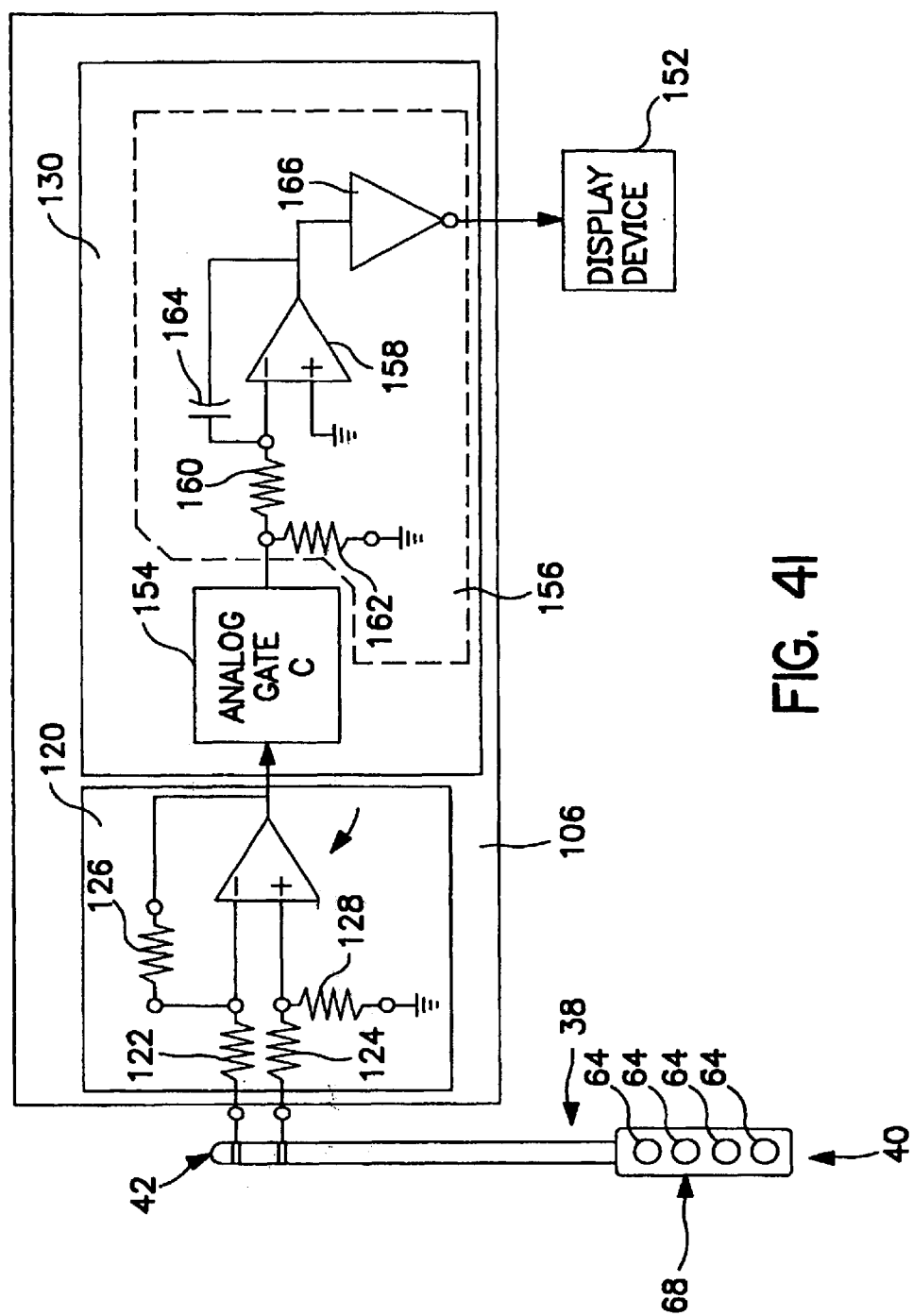
FIG. 41 is a schematic diagram showing an alternate embodiment of the control device of the present invention.

Referring to FIG. 41, an alternative embodiment of controller 130 includes an amplifier/filter 120, a conventional analog gate 154, an integrator 156 comprising an operational amplifier 158, resistors 160, 162 and a capacitor 164 connected as shown, as well as a sample and hold circuit 166. The output of integrator 156 is connected to display device 152.

Figure 42:
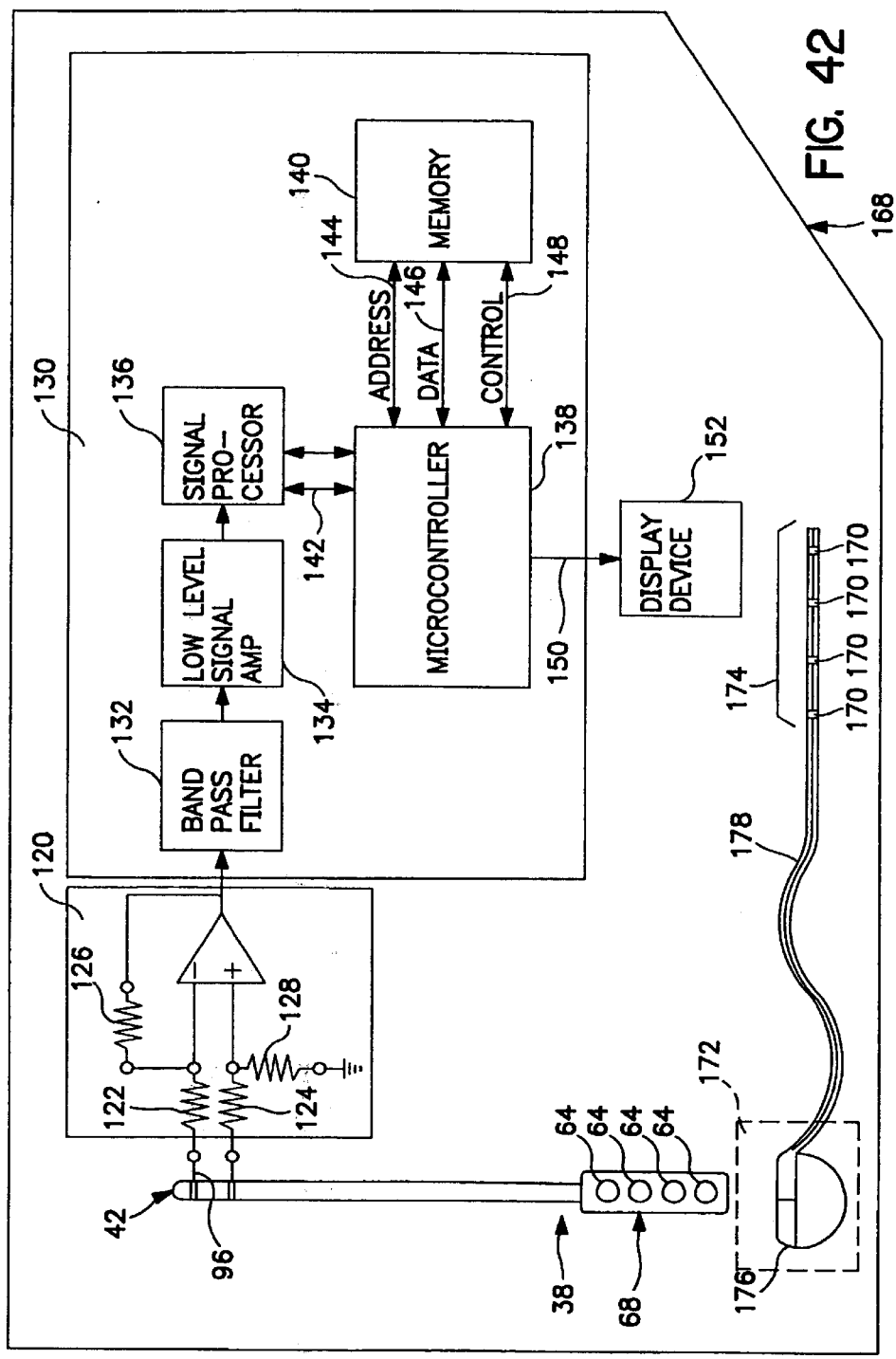
FIG. 42 is a schematic diagram showing an embodiment of the system of the present invention.
Figure 43:
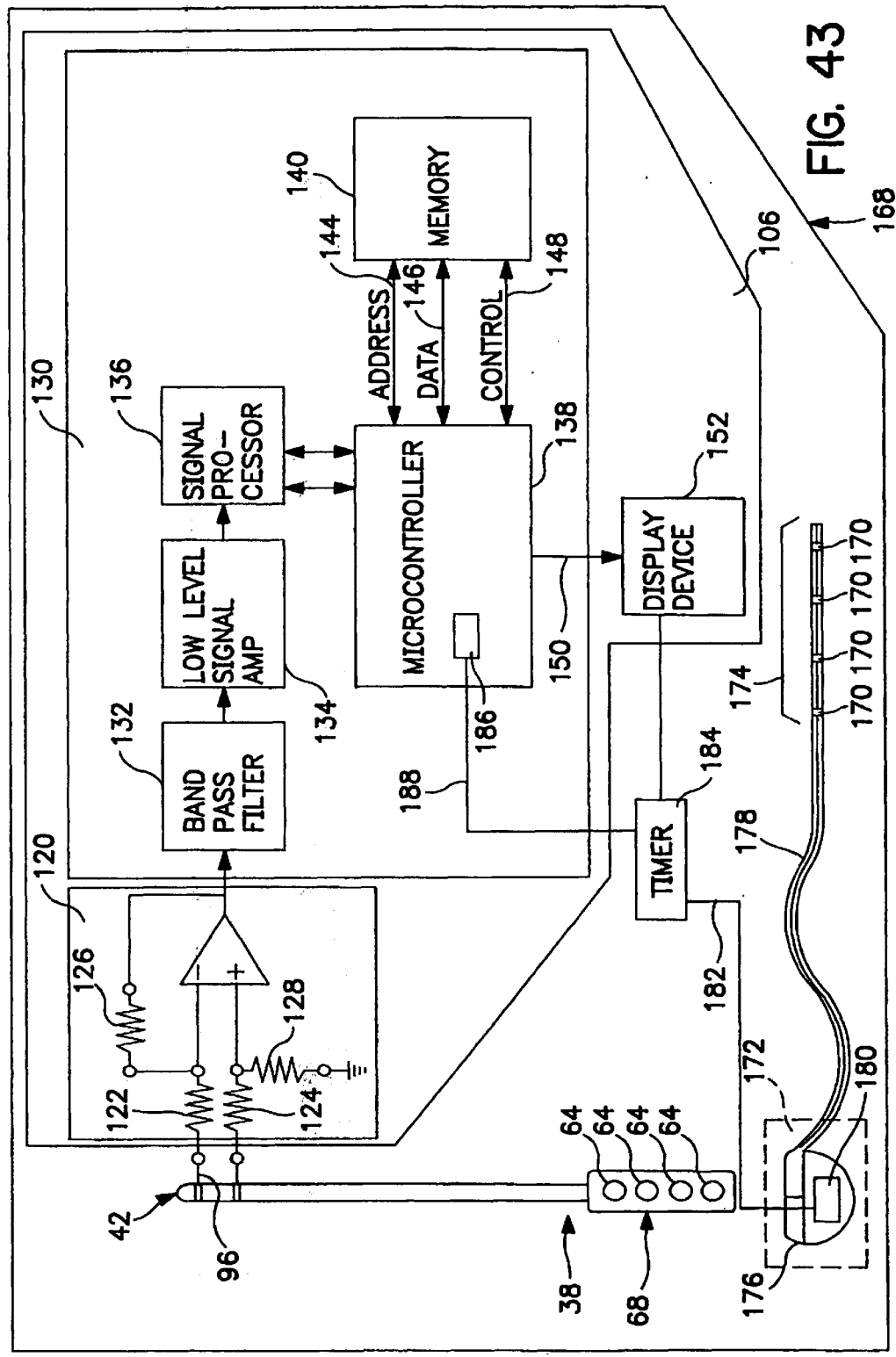
FIG. 43 is a schematic diagram showing an alternate embodiment of the system of the present invention.

In alternate embodiments of the invention shown in FIGS. 42 and 43, a system 168 is disclosed including probe 38. In system 168, stimulation electrodes 170 are used to create efferent nerve signals that are ultimately detected by distal recording electrodes 64 on probe 38. In these embodiments, probe 38 is as described above in all its embodiments. However, stimulation electrodes 170 and a stimulation system 172 for creating stimulation pulses are used to create the efferent nerve signals that are ultimately detected by distal recording electrodes 64.

Stimulation electrodes 170 are preferably part of a lead 174 such as a Pisces Quad lead sold by Medtronic, Inc. of Minneapolis, Minn. The Pisces Quad lead has for stimulating electrodes 170, each capable of being independently controlled. Lead 174 is implanted epidurally near the spinal cord or next to the sacral nerves by techniques well understood in the art as is described briefly below.

In these embodiments, stimulation system 172 includes a pulse generator 176 producing an output of electrical pulses. These pulses are provided to stimulation electrodes 170 through a series of connecting wires 178. Pulse generator 176 may be implantable pulse generators well known in the art such as those made by Medtronic, Inc. of Minneapolis, Minn. under the trademarks: Itrel II®, Itrel III®. Alternately, pulse generator 176 may be an RF powered system well known in the art such as those made by Medtronic, Inc. of Minneapolis, Minn. under the trademarks: X-trel® and Mattrix®. Regardless of the type of pulse generator 176 used, in this embodiment, stimulation is presented to spinal cord nerves or sacral nerves through stimulation electrodes 170 through a sequence of or continuous stream of electrical pulses. The effect of this stimulation is detected by distal recording electrodes 64.

In these embodiments of system 168, the effect of a sequence of or a continuous stream of electrical pulses applied to the spinal cord or sacral nerves is detected by distal recording electrodes 64. However, it is sometimes useful to measure the time that it takes for a particular electrical pulse or series of electrical pulses applied to the spinal cord or sacral nerves to manifest itself or themselves in electrical activity in the nerves of the pelvic floor. Therefore, it is sometimes desirable to time the application of an electric pulse or series of electrical pulses applied to the spinal cord or sacral nerve and the resulting manifestation of such stimulation by electrical activity in the nerves of the pelvic floor as detected by the distal recording electrodes 64.

To accomplish this timing, in the embodiment of FIG. 43, pulse generator 176 is modified to include a stimulation output circuit 180 that produces a timing signal along with the pulse or a series of pulses that is applied to stimulation electrodes 170. The timing signal indicates that the pulse or series of pulses has been applied to the stimulation electrodes 170 to stimulate the spinal cord or sacral nerves. The timing signal is applied through a stimulator timing wire 182 to a timer 184.

Control device 106 also has a detector output circuit 186 that that produces a signal when nerve activity is detected by distal recording electrodes 64. Output circuit 186 is connected to timer 184 through a detector timing wire 188. Timer 184 times the time difference between the signal produced by stimulation output circuit 180 and the signal produced by detector output circuit 186. The difference in timing between the signals sent from output circuit 180 from pulse generator 176 and the detector output circuit 186 from control device 106 indicates the time it took for an action potential generated by stimulation electrodes 170 to be detected by distal recording electrodes 64.

In the embodiments of the invention shown in FIGS. 42 and 43, the electrical voltage presented to stimulating electrodes 170 is adjustable in amplitude. At a certain amplitude, an action potential will be generated in either the spinal cord nerves or sacral nerves that will be manifest as electrical activity detected by the distal recording electrodes 64. The amplitude necessary to produce detectable nerve activity by distal recording electrodes 64 can be determined by the normal control function of the pulse generator 176. This amplitude may be useful to the attending physician in determining the condition of the nerves of the pelvic floor.

Dorsal column nerve fibers in the spinal cord typically conduct action potentials at a rate from about 100 meters per second down to 40 meters per second, although velocities might be slower if fibers become thinner as they ascend in the dorsal columns. For example, if distal recording electrodes 64 are located 10 cm from the stimulation electrodes 170, the compound action potentials from the stimulated nerve fibers would arrive at 1.0 millisecond from the end of the pulse applied by stimulation electrodes 170 for fibers conducting at 100 meters per second and at 2.5 milliseconds for fibers conducting at 40 meters per second. For sacral nerve stimulation, the fastest fibers may be efferent alpha-motor neurons. Any significant deviation in the conduction speed indicates a possible problem with the nerves of the pelvic floor.

During the surgical operation, the practitioner must position the stimulating electrodes 170 optimally either near the spinal cord or near sacral nerves. In this way, the level of electrical stimulation necessary to produce an action potential detectable in the pelvis or pelvic region by distal recording electrodes 64 can be determined. In addition, the presence or non-presence of electrical activity in selected regions of the pelvis or pelvic floor region in response to electrical stimulation by stimulating electrodes 170 can indicate the innervation and condition of nerves in the pelvis or pelvic floor region.

Operationally, stimulation lead 174 may also be placed near a sacral nerve by inserting a hollow needle through the skin and into a foramen containing the sacral nerve of interest. Thereafter, the stimulation lead 174 is passed through the needle to a desired location near the sacral nerve. Then, the needle is removed leaving the stimulation lead 40 in position near the sacral nerve. Alternately, the stimulation lead 174 may be placed near a sacral nerve of interest by performing a partial laminectomy. In a partial laminectomy, the sacrum is surgically opened and stimulation lead 174 placed near the sacral nerve of interest.

One or more stimulation leads 174 may be placed near the spinal cord or near selected sacral nerves as desired. In this way, various areas of the spinal cord or various sacral nerves can be electrically stimulated and the resulting electrical activity determined by distal recording electrodes 64. This also has the effect of determining unilateral and bilateral nerve response in the pelvic floor region.

Figure 44:
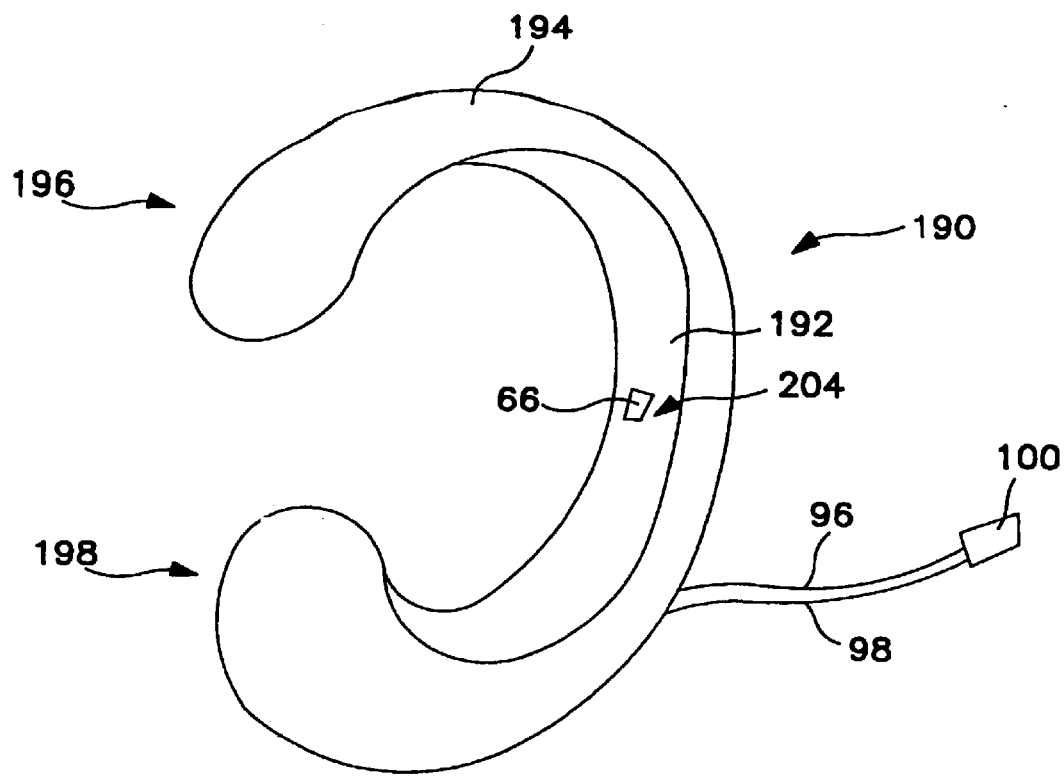
FIG. 44 is a perspective view of an alternate embodiment of the invention.
Figure 45:
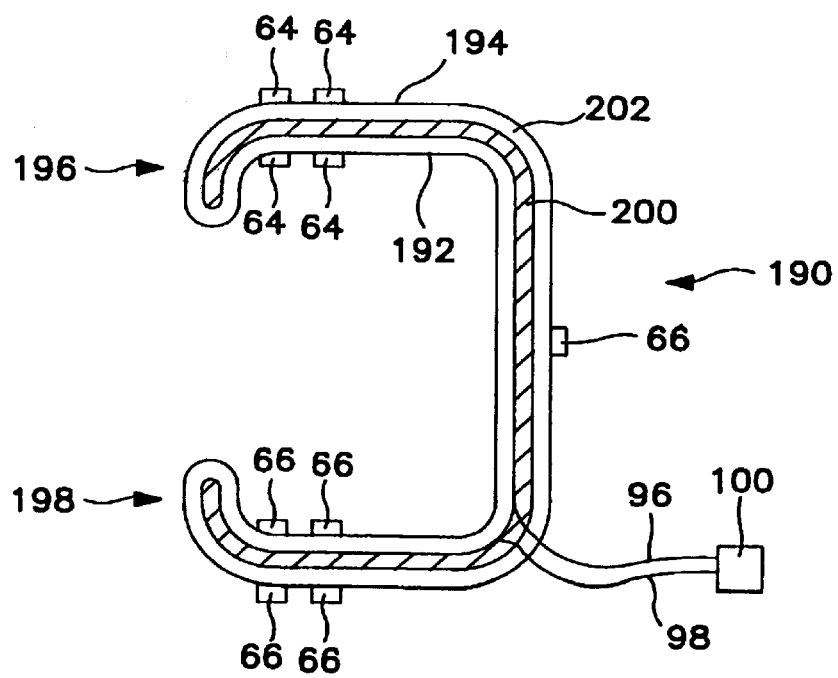
FIG. 45 is a side cross-sectional view of the embodiment of FIG. 44.

A further embodiment of the invention is shown in FIGS. 44–45. In this embodiment, a clip 190 is provided having an inner surface 192, an outer surface 194, a distal end 196 and a proximal end 198. Clip 190 is essentially "C" shaped and made of a material that biases clip 190 to maintain the "C" shape. Preferably, clip 190 is made of a first core 200 made of spring material such as spring steel or nitinol (nickel titanium alloy) although any other material that has the characteristics of resisting displacement and returning to its original unstressed configuration of spring steel or nitinol may also be used. It may be preferable to coat the first core 200 of clip 190 with a coat 202 of an insulating biocompatible material such as silicone, silicone rubber or polyurethane. Where first core 200 is made of an electrically conductive material such as spring steel, it is particularly desirable that coat 202 be made of an electrically insulating material, again such as silicone, silicone rubber or polyurethane. In this embodiment, coat 202 may be a biocompatible abrasion resistant inert, biocompatible, ceramic coating such as an oxide, nitride, or amorphous diamond-like carbon coating to electrically insulate the first core 200.

Distal recording electrodes 64 may be located on either the inner surface 192 or outer surface 194 of clip 190 at the distal end 196, proximal end 198 or anyplace between distal end 196 and proximal end 198. Wires 96, 98 connect distal recording electrodes 64 and proximal recording electrodes 66, respectively, to a connector 100.

Figure 48:
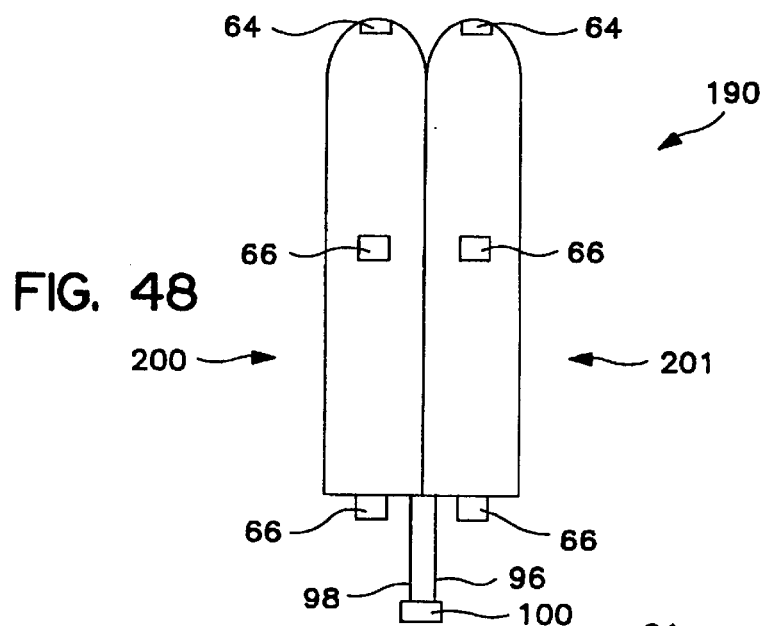
FIG. 48 is a side view of an alternate embodiment of the invention of FIG. 44.
Figure 49:
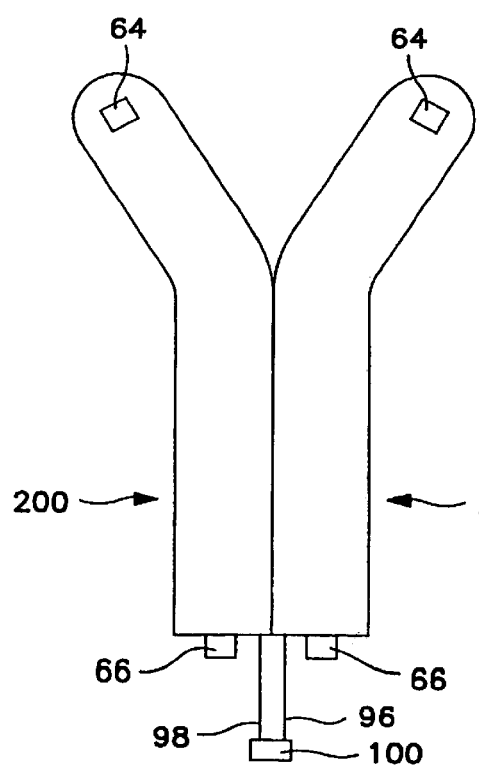
FIG. 49 is a side view of an alternate embodiment of the invention of FIG. 44.
Figure 50:
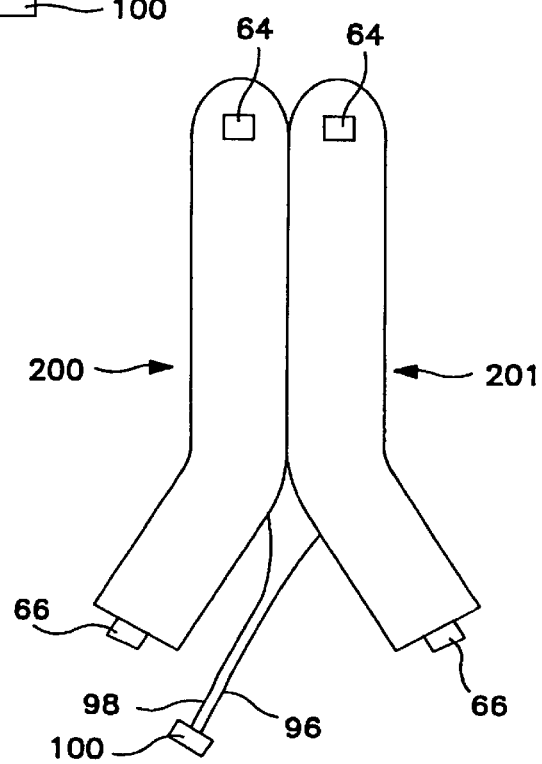
FIG. 50 is a side view of an alternate embodiment of the invention of FIG. 44.

Clip 190 may also be configured so as to have a second core 201, identical to or substantially similar to core 200 located next to core 200 in a side by side configuration. In this embodiment, shown in FIG. 48, core 200 and core 201 are joined at approximately their respective middle sections with their respective distal and proximal ends 196, 198 splayed away from each other. This allows distal and proximal recording electrodes 64, 66 to be located off the physiologic midline in contact with tissue. In a variant of this embodiment shown in FIG. 49, the distal ends 196 of cores 200, 201 are splayed away from each other while the proximal ends 198 are joined side by side along substantially their entire proximal length. In a further variant of this embodiment shown in FIG. 50, the proximal ends 198 of cores 200, 201 are splayed away from each other while the distal ends 196 are joined side by side along substantially their entire proximal length.

Figure 46:
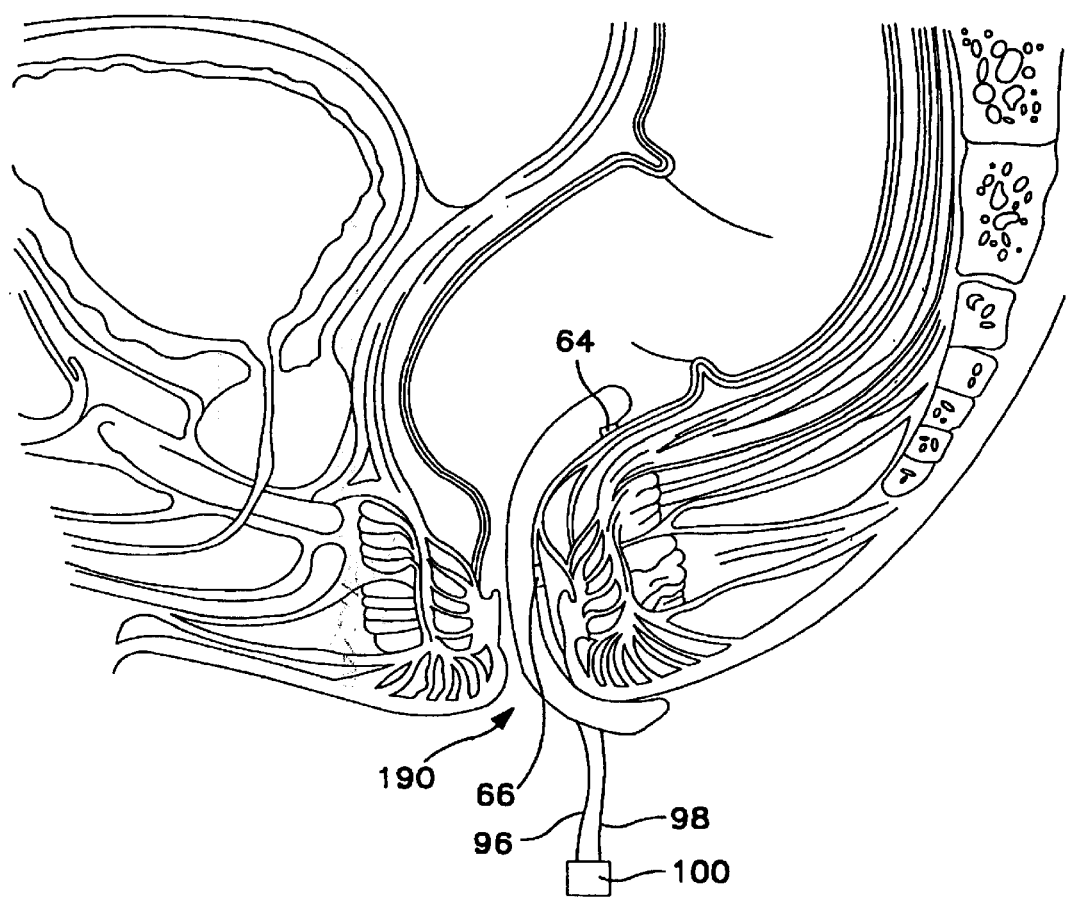
FIG. 46 is a sectional view of the embodiment of FIG. 44 in place in an anal canal.

In use as shown in FIG. 46, clip 190 may be placed in the anal canal 6 so that the distal end 196 is placed above the hemorrhoidal plexus 18 at point 20 where the rectum 4 widens. The proximal end 198 contacts the tissue outside the sphincter 16 near the anal verge 8. In this position, distal recording electrodes 64 also contact the tissue of the rectum 4 at point 20 where the rectum 4 widens above the hemorrhoidal plexus 18. Proximal recording electrodes 66, if present, will then contact the rectal tissue in the hemorrhoidal plexus 18 on the tissue of the submucous space 10 where the lack of karetin allows the proximal recording electrodes 66 to be in electrical contact with the tissue of the hemorrhoidal plexus 18.

Clip 190 is sized so that in the position described above and shown in FIG. 46, clip 190 is slightly distended from its relaxed position. In this configuration, the spring material of first core 200 biases the distal end 196 and the proximal end 198 into a slight "pushing" contact with the tissue of the anal canal 6 at point 20 and outside the sphincter 16. This "pushing" contact holds the clip 190 in place and holds distal recording electrodes 64 and proximal recording electrodes 66, if present, in contact with the tissue of the anal canal 6. In this position, the distal and proximal recording electrodes 64, 66 will be able to record electrical activity in the pelvic region as described above. Alternately, the spring material 200 may also be biased to move distal end 196 and proximal end 198 into "pinching" contact with the desired tissue.

Figure 47:
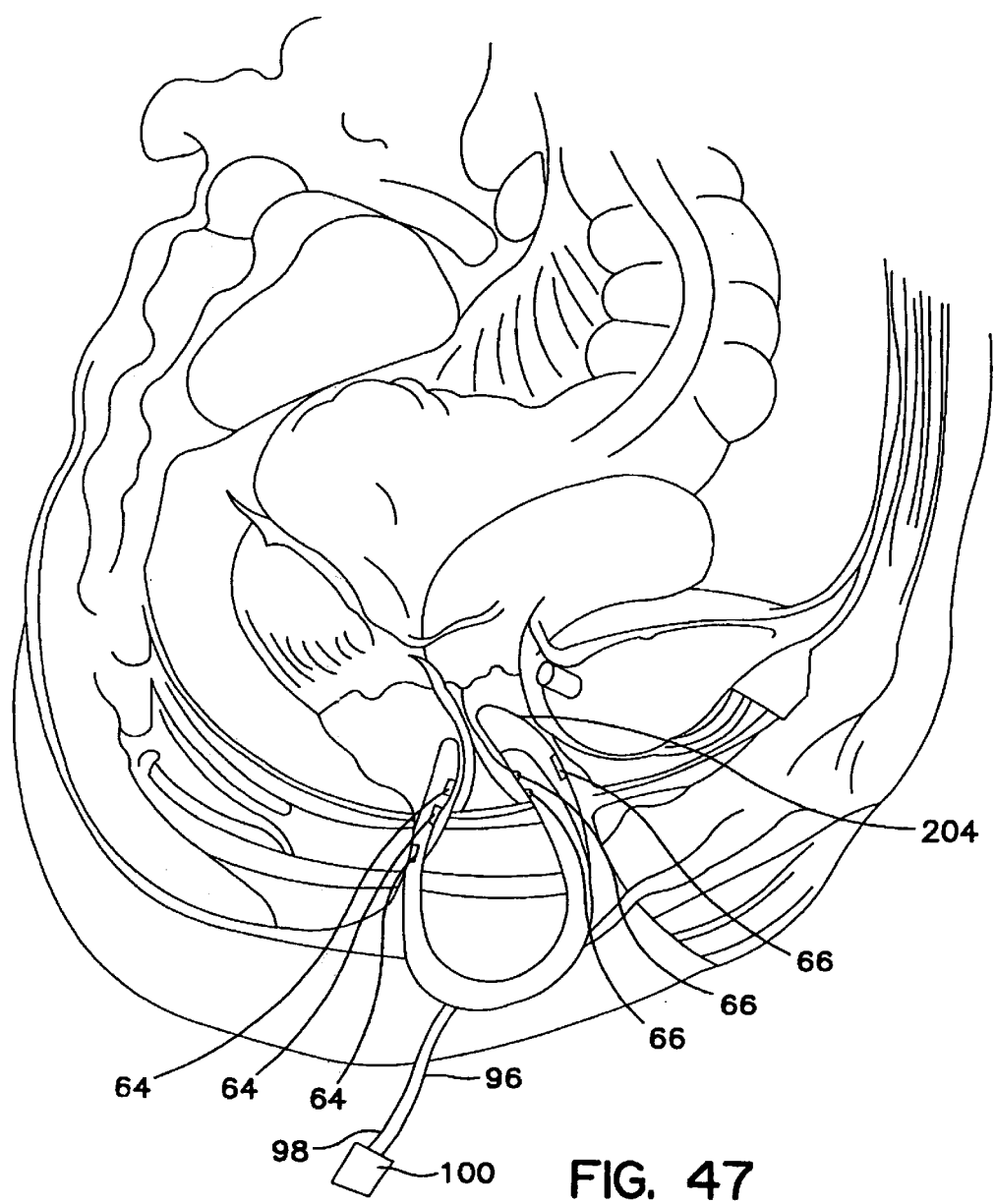
FIG. 47 is a sectional view of the embodiment of FIG. 44 in place in a vagina and an anal canal.

Clip 190 may also be place in both the vagina and rectum 4 as shown in FIG. 47. Here, clip 190 is as described above. However, clip 190 is placed so that either the distal end 196 or proximal end 198 is placed in the vagina 204 near the entrance to the vagina 204. The corresponding proximal end 198 or distal end 196, respectively, is then placed in the anal canal 6 in contact with the hemorrodal plexus 18. The spring material of first core 200 biases the distal end 196 and the proximal end 198 into either a slight "pushing" or "pinching" contact with the tissue of the anal canal 6 and vagina. This "pushing" or "pinching" contact holds the clip 190 in place and holds distal recording electrodes 64 and proximal recording electrodes 66, if present, in contact with the tissue of the anal canal 6 and vagina 204. In this position, the distal and proximal recording electrodes 64, 66 will be able to record electrical activity in the pelvic region as described above.

The invention described herein has been described primarily as a device for placement in the anal canal. However, it is to be understood that the invention may also be inserted and used vaginally. In this use, the invention will perform essentially as described above. However, slight modifications may be necessary to implement the invention in this application as will be clear to those skilled in the art. For example, locating structure 74 in all its embodiments may be modified to conform to the external configuration of the vagina.

While the invention has been described herein relative to a number of particularized embodiments, it is understood that modifications of, and alternatives to, these embodiments, such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A method of quantifying nerve and neural-muscular integrity related to pelvic organs or pelvic floor functions comprising:
   providing a probe comprising a body, a distensible member, and a recording electrode, wherein the distensible member has a first end connected to the body and a distal end movable relative to the body, and wherein the recording electrode is attached to the distensible member adjacent the distal end;
   placing the probe into the anal canal or vagina;
   moving the distal end of the distensible member away from the body to engage tissue of the anal canal or vagina with the recording electrode;
   placing a stimulation electrode, connected to a pulse generator, near the spinal cord or sacral nerves;
   producing electrical stimulation pulses at the stimulation electrode; and
   detecting the resulting electrical activity in the pelvic organs or pelvic floor by the recording electrode.

2. The method of claim 1 further comprising the step of timing the time between the application of a stimulation pulse by the stimulation electrode and the detection of the resulting electrical activity in the pelvic organs or pelvic floor by the recording electrode.

3. The method of claim 1 wherein moving the distal end of the distensible member away from the body to engage tissue of the anal canal or vagina comprises moving the distensible member away from the body to engage the mucosal tissue of the rectal wall, wherein the mucosal tissue of the rectal wall is pushed against the levator ani muscles.

4. The method of claim 1 wherein the distensible member comprises two or more wings each comprising a distal end, and wherein the moving step comprises moving the distal ends of the wings away from the body.

5. The method of claim 4 further comprising one or more additional recording electrodes, wherein a recording electrode is adjacent each wing, and wherein the moving step comprises moving each of the wings away from the body to engage tissue of the anal canal or vagina with the recording electrodes.

6. The method of claim 1 wherein the probe further comprises a distending member, wherein at least a portion of the distending member is positioned between the body and the distensible member, and wherein the moving step comprises distending the distending member thereby causing the distensible member to move away from the body.

7. The method of claim 6 wherein the distending member comprises a balloon, and wherein the moving step comprises expanding the balloon, wherein the balloon exerts pressure on the distensible member thereby causing the distensible member to move away from the body.

8. A method of quantifying nerve and neural-muscular integrity related to pelvic organs or pelvic floor functions comprising:

providing a probe comprising a body, a distensible member, and a recording electrode, wherein the distensible member has a first end connected so he body and a distal end movable relative to the body, and wherein the recording electrode is attached to the distensible member adjacent the distal end;

placing the probe into the anal canal or vagina;

moving the distal end of the distensible member away from the body to engage tissue of the anal canal or vagina with the recording electrode; and detecting the electrical activity in the pelvic organs or pelvic floor by the recording electrode.

9. A method of quantifying nerve and neural-muscular integrity related to pelvic organs or pelvic floor functions comprising:

providing a probe comprising a body, a plurality of wings, and at least one recording electrode, wherein each of the plurality of wings has a first end connected to the body and a distal end movable relative to the body, and wherein the at least one recording electrode is attached to one of the plurality of wings adjacent the distal end;

placing the probe into the anal canal or vagina;

moving the distal end of the plurality of wings away from the body to engage tissue of the anal canal or vagina with the at least one recording electrode; and detecting the electrical activity in the pelvic organs or pelvic floor by the at least one recording electrode.

10. The method of claim 9 wherein the plurality of wings comprises four wings, and the at least one recording electrode comprises four recording electrodes, wherein there is a recording electrode adjacent the distal end of each of the four wings, and wherein the moving step comprises moving the distal ends of the four recording electrodes away from the body to engage the tissue of the anal canal or vagina with the four recording electrodes.

11. The method of claim 9 wherein the probe further comprises a distending member, wherein at least a portion of the distending member is positioned between the body and one or more of the plurality of wings, and wherein the moving step comprises distending the distending member thereby causing one or more of the plurality of wings to move away from the body.

12. The method of claim 11 wherein the distending member comprises a balloon, and wherein the moving step comprises expanding the balloon, wherein the balloon exerts pressure on one or more wings thereby causing one or more wings to move away from the body.

13. The method of claim 12 wherein the step of expanding the balloon comprises forcing a fluid into the balloon.

14. The method of claim 13 wherein the body includes a lumen and the fluid is forced into the balloon through the lumen.

15. A method of quantifying nerve and neural-muscular integrity related to pelvic organs or pelvic floor functions comprising:

providing a probe comprising a body, a plurality of wings, and at least one recording electrode, wherein each of the plurality of wings has a first end connected to the body and a distal end movable relative to the body, and wherein the at least one recording electrode is attached to one of the plurality of wings adjacent the distal end;

placing the probe into the anal canal or vagina;

moving the distal end of the plurality of wings away from the body to engage tissue of the anal canal or vagina with the at least one recording electrode;

placing a stimulation electrode, connected to a pulse generator, near the spinal cord or sacral nerves;

producing electrical stimulation pulses at the stimulation electrode;

detecting the resulting electrical activity caused by the stimulation pulses at the stimulation electrode in the pelvic organs or pelvic floor by the at least one recording electrode.

* * * * *